(12) United States Patent
Chaudhuri

(10) Patent No.: US 10,030,233 B2
(45) Date of Patent: Jul. 24, 2018

(54) MODIFIED P450 REDUCTASE WITH N-TERMINAL DELETIONS AND ENDOPLASMIC RETICULUM RETENTION TAG

(71) Applicant: DE MONTFORT UNIVERSITY, Leicester, Leicestershire (GB)

(72) Inventor: Bhabatosh Chaudhuri, Leicester (GB)

(73) Assignee: DE MONTFORT UNIVERSITY, Leicester, Leicestershire (GB)

( * ) Notice: Subject to any disclaimer, the term of this patent is extended or adjusted under 35 U.S.C. 154(b) by 0 days.

(21) Appl. No.: 15/180,288

(22) Filed: Jun. 13, 2016

(65) Prior Publication Data

US 2016/0298090 A1 Oct. 13, 2016

Related U.S. Application Data

(63) Continuation of application No. PCT/GB2014/053669, filed on Dec. 11, 2014.

(30) Foreign Application Priority Data

Dec. 20, 2013 (GB) .................... 1322740.0

(51) Int. Cl.
*C12N 9/02* (2006.01)

(52) U.S. Cl.
CPC .... *C12N 9/0042* (2013.01); *C12Y 106/02004* (2013.01); *C07K 2319/04* (2013.01)

(58) Field of Classification Search
None
See application file for complete search history.

(56) References Cited

FOREIGN PATENT DOCUMENTS

| GB | 2485479 A | 5/2012 |
| WO | 2007129050 A2 | 11/2007 |
| WO | 2010134095 A2 | 11/2010 |

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
Accession P16435. Apr. 26, 2005.*
Singh et al. Curr Protein Pept Sci. 2017, 18, 1-11.*
Database UniProt [Online] Jul. 5, 2004 (Jul. 5, 2004), RecName: Full=NADPH—cytochrome P450 reductase XP002737970, retrieved from EBI accession No. UNIPROT:Q6PCH9, Database accession No. Q6PCH9, Klein, et al., "Genetic and genomic tools for Xenopus research: The NIH Xenopus Initiative", Developmental Dynamics, Wiley-Liss, Inc., 225(4):384-391, 2002.
Kargel, et al., "Candida Maltosana DPH-Cytochrome P450 Reductase: Cloning of a Full-Length CDNA, Heterologous Expression in *Saccharomyces cerevisiae* and Function of the N-Terminal Region for Membrane Anchoring and Proliferation of the Endoplasmic Reticulum", Yeast, John Wiley & Sons Ltd, 12(4):333-348, 1996.
Neve, et al., "Intracellular transport and localization of microsomal cytochrome P450", Analytical and Bioanalytical Chemistry, 392(6):1075-1084, 2008.
Semenza, et al., "Changing the specificity of the sorting receptor for luminal endoplasmic reticulum proteins", Journal of Molecular Biology, 224(1):1-5, 1992.
Pelham, et al., "Sorting of soluble ER proteins in yeast", Embo Journal, 7(6):1757-1762, 1988.
Peyronneau, et al., "Optimization of Yeast-Expressed Human Liver Cytochrome P450 3A4 Catalytic Activities by Coexpressing NADPH-Cytochrome P450 Reductase and Cytochrome B-5", European Journal of Biochemistry, 207(1): 109-116, 1992.

* cited by examiner

*Primary Examiner* — Christian Fronda
(74) *Attorney, Agent, or Firm* — Mahreen Chaudhry Hoda; Carolyn S. Elmore; Elmore Patent Law Group, P.C.

(57) ABSTRACT

The present invention provides an isolated or recombinant polypeptide comprising or consisting of a modified P450 reductase which lacks N-terminal amino acids relative to the corresponding wild type P450 reductase and comprises an epitope tag comprising the sequence HDEL or KDEL. The modified P450 reductase, when co-expressed with a cytochrome P450, increases the activity and/or expression of the cytochrome P450 compared to the activity and/or expression of the cytochrome P450 when co-expressed with the wild type P450 reductase.

8 Claims, 15 Drawing Sheets

```
                     10         20         30         40         50
                      *          *          *          *          *
hRD_PRT_677     MGDSHVDTSSTVSEAVAEEVSLFSMTDMILFSLIVGLLTYWFLFRKKKEE
delN1hRD_PRT    -----------------------MTDMILFSLIVGLLTYWFLFRKKKEE
delN2hRD_PRT    -------------------------------------------------

60         70         80         90        100
                      *          *          *          *          *
hRD_PRT_677     VPEFTKIQTLTSSVRESSFVEKMKRTGRNIIVFYGSQTGTAEEFANRLSK
delN1hRD_PRT    VPEFTKIQTLTSSVRESSFVEKMKRTGRNIIVFYGSQTGTAEEFANRLSK
delN2hRD_PRT    ---MTKIQTLTSSVRESSFVEKMKRTGRNIIVFYGSQTGTAEEFANRLSK 110        120        130        140        150
                      *          *          *          *          *
hRD_PRT_677     DAHRYGMRGMSADPEEYDLADLSSLPEIDNALVVFCMATYGEGDPTDNAQ
delN1hRD_PRT    DAHRYGMRGMSADPEEYDLADLSSLPEIDNALVVFCMATYGEGDPTDNAQ
delN2hRD_PRT    DAHRYGMRGMSADPEEYDLADLSSLPEIDNALVVFCMATYGEGDPTDNAQ 160        170        180        190        200
                      *          *          *          *          *
hRD_PRT_677     DFYDWLQETDVDLSGVKFAVFGLGNKTYEHFNAMGKYVDKRLEQLGAQRI
delN1hRD_PRT    DFYDWLQETDVDLSGVKFAVFGLGNKTYEHFNAMGKYVDKRLEQLGAQRI
delN2hRD_PRT    DFYDWLQETDVDLSGVKFAVFGLGNKTYEHFNAMGKYVDKRLEQLGAQRI 210        220        230        240        250
                      *          *          *          *          *
hRD_PRT_677     FELGLGDDDGNLEEDFITWREQFWPAVCEHFGVEATGEESSIRQYELVVH
delN1hRD_PRT    FELGLGDDDGNLEEDFITWREQFWPAVCEHFGVEATGEESSIRQYELVVH
delN2hRD_PRT    FELGLGDDDGNLEEDFITWREQFWPAVCEHFGVEATGEESSIRQYELVVH 260        270        280        290        300
                      *          *          *          *          *
hRD_PRT_677     TDIDAAKVYMGEMGRLKSYENQKPPFDAKNPFLAAVTTNRKLNQGTERHL
delN1hRD_PRT    TDIDAAKVYMGEMGRLKSYENQKPPFDAKNPFLAAVTTNRKLNQGTERHL
delN2hRD_PRT    TDIDAAKVYMGEMGRLKSYENQKPPFDAKNPFLAAVTTNRKLNQGTERHL 310        320        330        340        350
                      *          *          *          *          *
hRD_PRT_677     MHLELDISDSKIRYESGDHVAVYPANDSALVNQLGKILGADLDVVMSLNN
delN1hRD_PRT    MHLELDISDSKIRYESGDHVAVYPANDSALVNQLGKILGADLDVVMSLNN
delN2hRD_PRT    MHLELDISDSKIRYESGDHVAVYPANDSALVNQLGKILGADLDVVMSLNN 360        370        380        390        400
                      *          *          *          *          *
hRD_PRT_677     LDEESNKKHPFPCPTSYRTALTYYLDITNPPRTNVLYELAQYASEPSEQE
delN1hRD_PRT    LDEESNKKHPFPCPTSYRTALTYYLDITNPPRTNVLYELAQYASEPSEQE
delN2hRD_PRT    LDEESNKKHPFPCPTSYRTALTYYLDITNPPRTNVLYELAQYASEPSEQE 410        420        430        440        450
                      *          *          *          *          *
hRD_PRT_677     LLRKMASSSGEGKELYLSWVVEARRHILAILQDCPSLRPPIDHLCELLPR
delN1hRD_PRT    LLRKMASSSGEGKELYLSWVVEARRHILAILQDCPSLRPPIDHLCELLPR
delN2hRD_PRT    LLRKMASSSGEGKELYLSWVVEARRHILAILQDCPSLRPPIDHLCELLPR
```

FIG. 7

```
                    460        470        480        490        500
                     *          *          *          *          *
hRD_PRT_677     LQARYYSIASSSKVHPNSVHICAVVVEYETKAGRINKGVATNWLRAKEPA
delN1hRD_PRT    LQARYYSIASSSKVHPNSVHICAVVVEYETKAGRINKGVATNWLRAKEPA
delN2hRD_PRT    LQARYYSIASSSKVHPNSVHICAVVVEYETKAGRINKGVATNWLRAKEPA 510        520        530        540        550
                     *          *          *          *          *
hRD_PRT_677     GENGGRALVPMFVRKSQFRLPFKATTPVIMVGPCTGVAPFIGFIQERAWL
delN1hRD_PRT    GENGGRALVPMFVRKSQFRLPFKATTPVIMVGPCTGVAPFIGFIQERAWL
delN2hRD_PRT    GENGGRALVPMFVRKSQFRLPFKATTPVIMVGPCTGVAPFIGFIQERAWL 560        570        580        590        600
                     *          *          *          *          *
hRD_PRT_677     RQQGKEVGETLLYYGCRRSDEDYLYREELAQFHRDGALTQLNVAFSREQS
delN1hRD_PRT    RQQGKEVGETLLYYGCRRSDEDYLYREELAQFHRDGALTQLNVAFSREQS
delN2hRD_PRT    RQQGKEVGETLLYYGCRRSDEDYLYREELAQFHRDGALTQLNVAFSREQS 610        620        630        640        650
                     *          *          *          *          *
hRD_PRT_677     HKVYVQHLLKQDREHLWKLIEGGAHIYVCGDARNMARDVQNTFYDIVAEL
delN1hRD_PRT    HKVYVQHLLKQDREHLWKLIEGGAHIYVCGDARNMARDVQNTFYDIVAEL
delN2hRD_PRT    HKVYVQHLLKQDREHLWKLIEGGAHIYVCGDARNMARDVQNTFYDIVAEL 660        670
                     *          *
hRD_PRT_677     GAMEHAQAVDYIKKLMTKGRYSLDVWS
delN1hRD_PRT    GAMEHAQAVDYIKKLMTKGRYSLDVWS
delN2hRD_PRT    GAMEHAQAVDYIKKLMTKGRYSLDVWS
```

FIG. 7 CONT'D

|              | 10         | 20         | 30         | 40         | 50 |
|---|---|---|---|---|---|

```
                         10         20         30         40         50
                          *          *          *          *          *
hRD_PRT_677        MGDSHVDTSSTVSEAVAEEVSLFSMTDMILFSLIVGLLTYWFLFRKKKEE
delN1hRD-M_PRT     -----------------------MTDMILFSLIVGLLTYWFLFRKKKEE
delN1hRD-HDEL_PR   -----------------------MTDMILFSLIVGLLTYWFLFRKKKEE
delN2hRD-HDEL_PR   -------------------------------------------------

60         70         80         90        100
                          *          *          *          *          *
hRD_PRT_677        VPEFTKIQTLTSSVRESSFVEKMRKTGRNIIVFYGSQTGTAEEFANRLSK
delN1hRD-M_PRT     VPEFTKIQTLTSSVRESSFVEKMRKTGRNIIVFYGSQTGTAEEFANRLSK
delN1hRD-HDEL_PR   VPEFTKIQTLTSSVRESSFVEKMRKTGRNIIVFYGSQTGTAEEFANRLSK
delN2hRD-HDEL_PR   ----MTKIQTLTSSVRESSFVEKMRKTGRNIIVFYGSQTGTAEEFANRLSK 110        120        130        140        150
                          *          *          *          *          *
hRD_PRT_677        DAHRYGMRGMSADPEEYDLADLSSLPEIDNALVVFCMATYGEGDPTDNAQ
delN1hRD-M_PRT     DAHRYGMRGMSADPEEYDLADLSSLPEIDNALVVFCMATYGEGDPTDNAQ
delN1hRD-HDEL_PR   DAHRYGMRGMSADPEEYDLADLSSLPEIDNALVVFCMATYGEGDPTDNAQ
delN2hRD-HDEL_PR   DAHRYGMRGMSADPEEYDLADLSSLPEIDNALVVFCMATYGEGDPTDNAQ 160        170        180        190        200
                          *          *          *          *          *
hRD_PRT_677        DFYDWLQETDVDLSGVKFAVFGLGNKTYEHFNAMGKYVDKRLEQLGAQRI
delN1hRD-M_PRT     DFYDWLQETDVDLSGVKFAVFGLGNKTYEHFNAMGKYVDKRLEQLGAQRI
delN1hRD-HDEL_PR   DFYDWLQETDVDLSGVKFAVFGLGNKTYEHFNAMGKYVDKRLEQLGAQRI
delN2hRD-HDEL_PR   DFYDWLQETDVDLSGVKFAVFGLGNKTYEHFNAMGKYVDKRLEQLGAQRI 210        220        230        240        250
                          *          *          *          *          *
hRD_PRT_677        FELGLGDDDGNLEEDFITWREQFWPAVCEHFGVEATGEESSIRQYELVVH
delN1hRD-M_PRT     FELGLGDDDGNLEEDFITWREQFWPAVCEHFGVEATGEESSIRQYELVVH
delN1hRD-HDEL_PR   FELGLGDDDGNLEEDFITWREQFWPAVCEHFGVEATGEESSIRQYELVVH
delN2hRD-HDEL_PR   FELGLGDDDGNLEEDFITWREQFWPAVCEHFGVEATGEESSIRQYELVVH 260        270        280        290        300
                          *          *          *          *          *
hRD_PRT_677        TDIDAAKVYMGEMGRLKSYENQKPPFDAKNPFLAAVTTNRKLNQGTERHL
delN1hRD-M_PRT     TDIDAAKVYMGEMGRLKSYENQKPPFDAKNPFLAAVTTNRKLNQGTERHL
delN1hRD-HDEL_PR   TDIDAAKVYMGEMGRLKSYENQKPPFDAKNPFLAAVTTNRKLNQGTERHL
delN2hRD-HDEL_PR   TDIDAAKVYMGEMGRLKSYENQKPPFDAKNPFLAAVTTNRKLNQGTERHL 310        320        330        340        350
                          *          *          *          *          *
hRD_PRT_677        MHLELDISDSKIRYESGDHVAVYPANDSALVNQLGKILGADLDVVMSLNN
delN1hRD-M_PRT     MHLELDISDSKIRYESGDHVAVYPANDSALVNQLGKILGADLDVVMSLNN
delN1hRD-HDEL_PR   MHLELDISDSKIRYESGDHVAVYPANDSALVNQLGKILGADLDVVMSLNN
delN2hRD-HDEL_PR   MHLELDISDSKIRYESGDHVAVYPANDSALVNQLGKILGADLDVVMSLNN 360        370        380        390        400
                          *          *          *          *          *
hRD_PRT_677        LDEESNKKHPFPCPTSYRTALTYYLDITNPPRTNVLYELAQYASEPSEQE
delN1hRD-M_PRT     LDEESNKKHPFPCPTSYRTALTYYLDITNPPRTNVLYELAQYASEPSEQE
delN1hRD-HDEL_PR   LDEESNKKHPFPCPTSYRTALTYYLDITNPPRTNVLYELAQYASEPSEQE
delN2hRD-HDEL_PR   LDEESNKKHPFPCPTSYRTALTYYLDITNPPRTNVLYELAQYASEPSEQE
```

FIG. 8

```
                    410        420        430        440        450
                     *          *          *          *          *
hRD_PRT_677      LLRKMASSSGEGKELYLSWVVEARRHILAILQDCPSLRPPIDHLCELLPR
delN1hRD-M_PRT   LLRKMASSSGEGKELYLSWVVEARRHILAILQDCPSLRPPIDHLCELLPR
delN1hRD-HDEL_PR LLRKMASSSGEGKELYLSWVVEARRHILAILQDCPSLRPPIDHLCELLPR
delN2hRD-HDEL_PR LLRKMASSSGEGKELYLSWVVEARRHILAILQDCPSLRPPIDHLCELLPR 460        470        480        490        500
                     *          *          *          *          *
hRD_PRT_677      LQARYYSIASSSKVHPNSVHICAVVVEYETKAGRINKGVATNWLRAKEPA
delN1hRD-M_PRT   LQARYYSIASSSKVHPNSVHICAVVVEYETKAGRINKGVATNWLRAKEPA
delN1hRD-HDEL_PR LQARYYSIASSSKVHPNSVHICAVVVEYETKAGRINKGVATNWLRAKEPA
delN2hRD-HDEL_PR LQARYYSIASSSKVHPNSVHICAVVVEYETKAGRINKGVATNWLRAKEPA 510        520        530        540        550
                     *          *          *          *          *
hRD_PRT_677      GENGGRALVPMFVRKSQFRLPFKATTPVIMVGPGTGVAPFIGFIQERAWL
delN1hRD-M_PRT   GENGGRALVPMFVRKSQFRLPFKATTPVIMVGPGTGVAPFIGFIQERAWL
delN1hRD-HDEL_PR GENGGRALVPMFVRKSQFRLPFKATTPVIMVGPGTGVAPFIGFIQERAWL
delN2hRD-HDEL_PR GENGGRALVPMFVRKSQFRLPFKATTPVIMVGPGTGVAPFIGFIQERAWL 560        570        580        590        600
                     *          *          *          *          *
hRD_PRT_677      RQQGKEVGETLLYYGCRRSDEDYLYREELAQFHRDGALTQLNVAFSREQS
delN1hRD-M_PRT   RQQGKEVGETLLYYGCRRSDEDYLYREELAQFHRDGALTQLNVAFSREQS
delN1hRD-HDEL_PR RQQGKEVGETLLYYGCRRSDEDYLYREELAQFHRDGALTQLNVAFSREQS
delN2hRD-HDEL_PR RQQGKEVGETLLYYGCRRSDEDYLYREELAQFHRDGALTQLNVAFSREQS 610        620        630        640        650
                     *          *          *          *          *
hRD_PRT_677      HKVYVQHLLKQDREHLWKLIEGGAHIYVCGDARNMARDVQNTFYDIVAEL
delN1hRD-M_PRT   HKVYVQHLLKQDREHLWKLIEGGAHIYVCGDARNMARDVQNTFYDIVAEL
delN1hRD-HDEL_PR HKVYVQHLLKQDREHLWKLIEGGAHIYVCGDARNMARDVQNTFYDIVAEL
delN2hRD-HDEL_PR HKVYVQHLLKQDREHLWKLIEGGAHIYVCGDARNMARDVQNTFYDIVAEL 660        670
                     *          *
hRD_PRT_677      GAMEHAQAVDYIKKLMTKGRYSLDVWS------------------
delN1hRD-M_PRT   GAMEHAQAVDYIKKLMTKGRYSLDVWSSSEQKLISEEDLNGSRL
delN1hRD-HDEL_PR GAMEHAQAVDYIKKLMTKGRYSLDVWSHDEL--------------
delN2hRD-HDEL_PR GAMEHAQAVDYIKKLMTKGRYSLDVWSHDEL--------------
```

FIG. 8 CONT'D

```
   1  GGATCCAAAA AAATGACTGA TATGATTTTG TTCTCTTTGA TTGTCGGTTT GTTAACATAT
  61  TGGTTCTTGT TTAGGAAGAA GAAGGAGGAG GTCCCTGAGT TTACAAAAAT TCAGACATTG
 121  ACATCATCTG TCAGAGAGTC TTCATTCGTT GAAAAGATGA AGAAGACAGG TAGGAATATT
 181  ATAGTTTTCT ACGGATCTCA GACTGGTACT GCAGAGGAGT TCGCAAACAG GTTGTCTAAG
 241  GACGCACACA GGTACGGTAT GAGGGGAATG TCAGCAGACC CTGAGGAATA CGATTTGGCT
 301  GACTTATCTT CTTTGCCAGA GATTGACAAC GCTTTAGTCG TCTTCTGCAT GGCAACATAC
 361  GGTGAGGGTG ACCCTACAGA CAACGCTCAG GATTTCTACG ACTGGTTGCA GGAGACAGAC
 421  GTTGATTTGT CTGGTGTCAA ATTCGCTGTT TTTGGATTGG GAAATAAGAC TTACGAGCAC
 481  TTTAACGCTA TGGGTAAGTA CGTCGACAAA AGGTTGGAAC AGTTAGGTGC ACAGAGAATT
 541  TTCGAATTGG GATTGGGTGA CGACGATGGA AACTTGGAGG AGGACTTCAT TACATGGAGG
 601  GAGCAGTTCT GGCCAGCTGT CTGTGAACAT TTCGGTGTCG AGGCTACTGG TGAAGAATCA
 661  TCAATAAGGC AGTACGAGTT AGTCGTCCAC ACAGACATAG ACGCAGCTAA GGTCTACATG
 721  GGTGAAATGG GTAGATTGAA GTCATATGAA AATCAAAAAC CACCATTCGA CGCTAAGAAT
 781  CCATTCTTGG CAGCAGTCAC AACAAACAGG AAATTGAACC AGGGTACTGA GAGGCATTTG
 841  ATGCACTTGG AGTTGGACAT ATCTGATTCA AAAATTAGAT ACGAGTCTGG AGACCACGTC
 901  GCTGTCTACC CAGCAAATGA CTCTCGCATTG GTCAACCAGT TGGGAAAGAT TTTGGGTGCA
 961  GACTTGGACG TCGTCATGTC ATTGAACAAC TTGGATGAAG AGTCTAACAA GAAGCACCCA
1021  TTCCCATGCC CAACTTCTTA CAGGACTGCA TTAACATACT ACTTAGACAT TACTAACCCA
1081  CCTAGAACAA ATGTCTTATA CGAATTGGCT CAGTACGCAT CTGAACCATC AGAGCAAGAG
1141  TTGTTAAGAA AGATGGCATC TTCTTCTGGT GAGGGAAAGG AGTTGTATTT GTCTTGGGTC
1201  GTTGAGGCTA GAAGGCACAT ATTGGCTATA TTGCAGGACT GCCCATCTTT GAGGCCTCCA
1261  ATAGACCACT TATGCGAGTT ATTACCTAGA TTGCAAGCAA GATACTATTC TATTGCTTCA
1321  TCATCAAAGG TTCACCCAAA TTCTGTCCAC ATATGCGCTG TCGTCGTCGA GTATGAGACT
1381  AAGGCTGGAA GAATAAATAA GGGTGTCGCT ACAAACTGGT TAAGGGCTAA GGAGCCAGTC
1441  GGTGAGAACG GAGGTAGAGC TTTGGTTCCA ATGTTCGTCA GGAAATCACA GTTGAGGTTG
1501  CCTTTCAAGG CAACAACACC TGTCATTATG GTCGGTCCAG GTACAGGTTG GCACCCTTTC
1561  ATTGGTTTTA TACAGGAGAG AGCATGGTTA AGGCAGCAGG GTAAGGAAGT CGGTGAAACT
1621  TTGTTGTATT ACGGTTGCAG GAGGTCTGAC GAGGACTACT TGTATAGGGA GGAGTTGGCT
1681  CAATTCCACA GGGACGGTGC TTTGACACAA TTGAACGTTG CATTTAGCAG GGAGCAATCT
1741  CATAAAGTTT ATGTTCAACA TTTGTTAAAG CAAGACAGGG AGCACTTGTG GAAGTTGATA
1801  GAGGGAGGAG CTCACATATA CGTCTGTGGA GACGCTAGGA ACATGGCAAG GGACGTCCAG
1861  AATACATTTT ATGACATTGT CGCAGAGTTG GGTGCAATGG AGCACGCTCA AGCAGTTGAT
1921  TATATCAAGA AGTTGATGAC TAAAGGTAGA TACTCATTAG ACGTCTGGTC TTCATCAGAA
1981  CAGAAGTTAA TATCTGAGGA AGACTTAAAC GGTTCTAGGT TGTAATAGTCTAG A
```

FIG. 9

FIG. 13
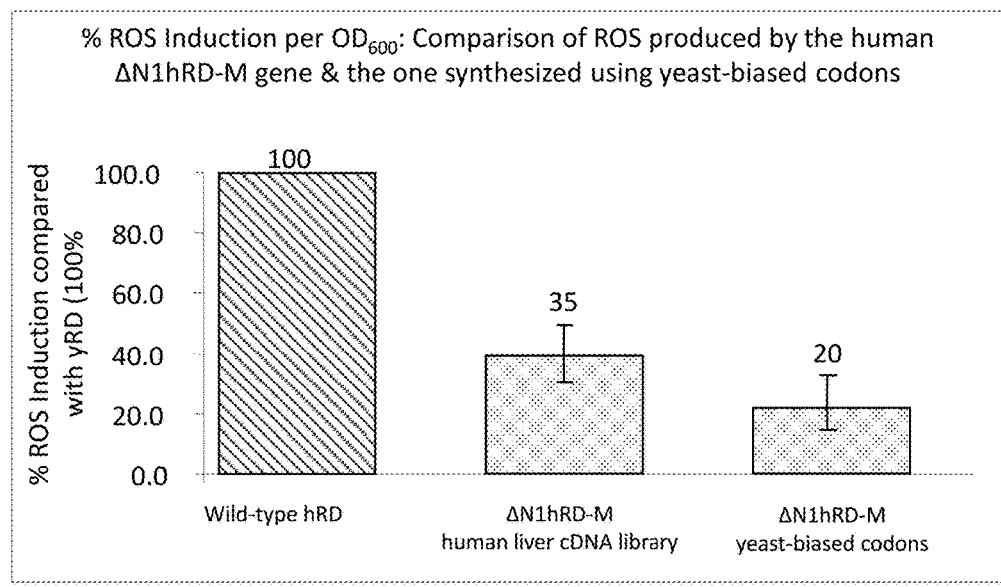
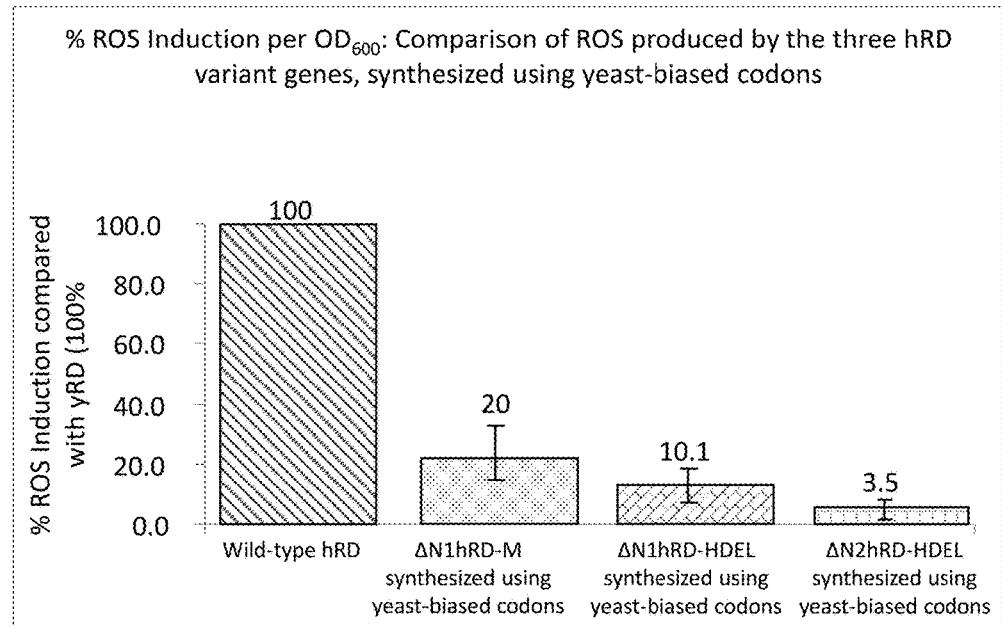
FIG. 14

MODIFIED P450 REDUCTASE WITH N-TERMINAL DELETIONS AND ENDOPLASMIC RETICULUM RETENTION TAG

RELATED APPLICATIONS

This application is a continuation of International Application No. PCT/GB2014/053669, which designated the United States and was filed on Dec. 11, 2014, published in English.

This application claims priority under 35 U.S.C. § 119 or 365 to Great Britain, Application No. 1322740.0, filed Dec. 20, 2013.

The entire teachings of the above applications are incorporated herein by reference.

The present invention relates to methods of expressing proteins. In particular, the present invention relates to cytochrome P450 expression systems and to the production of cytochrome P450 reductase (CPR).

Cytochrome P450 (CYP) belongs to a large family of detoxifying enzymes (present in different parts of the human body especially in the liver, kidneys, lung, the central nervous system) that is involved in the break-up (i.e. metabolism) of diverse xenobiotics, which include most pharmaceuticals, many dietary substances and a wide variety of environmental chemicals. Xenobiotics are defined as alien chemical substances that are introduced into the human organism either accidentally or deliberately. CYPs are involved in 90% of the metabolism of xenobiotics that occurs in the human body. CYPs metabolise xenobiotics by the action of oxygen, which makes them more soluble and easier to excrete.

During the drug development process, it is imperative that the rate of metabolism, and the nature and toxicity of the products is determined before a compound is introduced in human clinical trials. The present main commercial use of CYPs is for the investigation of the metabolism of drug compounds that are already in development. The CYPs are mostly used sparingly (because of high costs) in secondary assays to confirm a metabolic pathway. However, the use of CYPs to screen a vast number of potential drug candidates in pre-clinical research could greatly reduce the cost to pharmaceutical companies of late stage drug development failures.

There therefore exists a need to develop an improved system for expressing CYPs with high activities and/or at high expression levels to enable screening of drug compounds and in particular drug candidates for toxicity.

Human P450 reductase (hRD) is an enzyme that is anchored to the endoplasmic reticular (ER) membranes and acts as a co-factor which is essential for the activity of the cytochrome P450 isozymes. Unusually, as a co-factor, P450 reductase possesses enzymatic activity. It is essential for the activity of ER-membrane bound cytochrome P450 (CYP) enzymes. For recombinant expression of an ER-membrane bound CYP enzyme, P450 reductase needs to be co-produced.

A cytochrome P450 reductase from any organism abstracts electrons from NADPH and transfers them to the active site of a CYP so that divalent oxygen can become reactive to form reactive oxygen species (ROS). The ROS are used to add an —O— to un-reactive carbon atoms.

CPRs are naturally toxic to living cells because they are constantly involved in the production of ROS. Even a slight over-production of ROS kills the cells that are used to co-produce a CYP and CPR. This creates a problem for the recombinant over-expression of a CYP as it results in extremely low yields of the recombinant CYP.

A form of P450 reductase with reduced toxicity is known in the art from WO2007/129050. This modified reductase did not include N-terminal amino acids of the wild type reductase. The truncated reductase is soluble, i.e. it is not integrated into the ER membranes although it possesses reductase activity. In addition, a 12-amino acid c-myc tag was added to the 3'-end of the reductase.

In a first aspect, the present invention provides an isolated or recombinant polypeptide comprising or consisting of:
 a modified P450 reductase which lacks N-terminal amino acids relative to the corresponding wild type P450 reductase and comprises an epitope tag comprising the sequence HDEL (SEQ ID NO: 1) or KDEL (SEQ ID NO: 2),
 wherein the modified P450 reductase, when co-expressed with a cytochrome P450, increases the activity and/or expression of the cytochrome P450 compared to the activity and/or expression of the cytochrome P450 when co-expressed with the wild type P450 reductase.

Unexpectedly, it has been found that the soluble P450 reductase of WO2007/129050 (which is not membrane integrated) was retained in the ER by the addition of the C-terminal 12-amino acid c-myc tag peptide sequence. This was not appreciated in WO2007/129050. Accordingly, the invention provides alternative forms of modified P450 reductase that have ER retention signals. These P450 reductases give improved yields and CYP activity. Polypeptides of the invention are membrane integrated enzymes because they can be isolated from microsomes. They cause less ROS formation than wild-type reductase or the soluble reductase of WO2007/129050. Hence co-expression of polypeptides of the invention with a CYP yields more CYPs. Furthermore, polypeptides of the invention yield higher CYP activities than wild-type reductases; hence, they couple to CYPs better than wild-type reductase.

The activity of cytochrome P450 may be measured by the EROD assay or by other assays known in the art. The expression of cytochrome P450 may be measured using CO-difference spectra as is known in the art and is described in the examples herein.

P450 reductases of the invention may lack N-terminal amino acids by being truncated at the N terminus. The truncation may comprise the N-terminal membrane anchor sequence, which may comprise the 24 N-terminal amino acids. The deletion of this sequence results in the formation of a soluble P450 reductase protein, i.e. the protein does not integrate to the endoplasmic reticular membranes. A total of 54 amino acid acids may be truncated from the N-terminal. This deleted 54-amino acid domain has been described in the prior art as a membrane anchoring domain for hRD.

The epitope tag may be linked to the C-terminal end of the polypeptide, either via a linker or preferably directly. The linker may comprise two serine and/or glycine residues.

The P450 reductase may be a human P450 reductase. The polypeptide of the invention may comprise or consist of the amino acid sequence shown in FIG. 8 and labelled as "delN1hRD-HDEL_PR" (lacking 24 N-terminal amino acid residues—SEQ ID NO: 3) or the amino acid sequence shown in FIG. 8 and labelled as "delN2hRD-HDEL_PR" (lacking 54 N-terminal amino acid residues—SEQ ID NO: 4). The invention also provides polypeptides that comprise or consist of the amino acid sequence shown in FIG. 8 and labelled as "delN1hRD-HDEL_PR" (lacking 24 N-terminal amino acid residues) or the amino acid sequence shown in FIG. 8 and labelled as "delN2hRD-HDEL_PR" (lacking 54

N-terminal amino acid residues), wherein the amino acid sequence HDEL (SEQ ID NO: 1) is replaced by the sequence KDEL (SEQ ID NO: 2).

The HDEL epitope tag is a yeast ER retention signal. Accordingly, polypeptides of the invention comprising this tag may be expressed in yeast cells. When coexpressed with a cytochrome P450, the levels and activities of CYP are increased.

The wild type yeast P450 reductase (yRD) couples to human and plant CYPs far better than hRD during production in yeast. Unfortunately, yRD is far more toxic than hRD because the ROS produced by yRD dramatically reduce the levels of recombinant CYPs. Therefore, the P450 reductase may be a yeast P450 reductase. Such a reductase can improve not only yeast-based human CYP production systems in general but can also facilitate production of plant CYPs in yeast for bio-transformations. Baker's yeast is a unicellular eukaryote that mimics human cells.

Furthermore, the P450 reductase may be a non-human mammalian P450 reductase (such as from rodents such as guinea-pig, hamster, mouse, rabbit, rat. Alternatively, the P450 reductase may be from plants or fungi. Sequences of these P450 reductases are available from the NCBI database.

P450 reductases of the present invention may be used in the production of cytochrome P450 enzymes in yeast cells, as well as in insect and mammalian cells.

Polypeptides which include one or more additions, deletions, substitutions or the like relative to the polypeptides described above, such as homologues and fragments, are encompassed by the present invention. In addition, it may be possible to replace one amino acid with another of similar "type". For instance, a hydrophobic amino acid may be replaced with another. In the case of such altered polypeptides, the degree of identity with a polypeptide as described herein is less important than that the function of the polypeptide is retained. However, suitably, homologues having at least 60% identity with the polypeptide sequences described herein are provided and are encompassed by the present invention. Preferably, homologues having at least 70% identity, more preferably at least 80% identity are provided. Most preferably, homologues having at least 85%, 90%, 95%, 96%, 97%, 98% or even 99% or greater identity are provided.

The "percent identity" of two amino acid sequences or of two nucleic acid (nucleotide) sequences is generally determined by aligning the sequences for optimal comparison purposes (e.g., gaps can be introduced in either sequences for best alignment with the other sequence) and comparing the amino acid residues or nucleotides at corresponding positions. The "best alignment" is an alignment of two sequences that results in the highest percent identity. The percent identity is determined by the number of identical amino acid residues or nucleotides in the sequences being compared (i.e., % identity=# of identical positions/total # of positions×100).

The determination of percent identity between two sequences can be accomplished using a mathematical algorithm known to those of skill in the art. An example of a mathematical algorithm for comparing two sequences is the algorithm of Karlin and Altschul (1990) Proc. Natl. Acad. Sci. USA 87:2264-2268, modified as in Karlin and Altschul (1993) Proc. Natl. Acad. Sci. USA 90:5873-5877. The NBLAST and)(BLAST programs of Altschul, et al. (1990) J. Mol. Biol. 215:403-410 have incorporated such an algorithm. BLAST nucleotide searches can be performed with the NBLAST program, score=100, wordlength=12 to obtain nucleotide sequences homologous to a nucleic acid molecules of the invention. BLAST protein searches can be performed with the)(BLAST program, score=50, wordlength=3 to obtain amino acid sequences homologous to a protein molecules of the invention. To obtain gapped alignments for comparison purposes, Gapped BLAST can be utilized as described in Altschul et al. (1997) Nucleic Acids Res. 25:3389-3402. Alternatively, PSI-Blast can be used to perform an iterated search which detects distant relationships between molecules (Id.). When utilizing BLAST, Gapped BLAST, and PSI-Blast programs, the default parameters of the respective programs (e.g.,)(BLAST and NBLAST) can be used. See http://www.ncbi.nlm.nih.gov. Another example of a mathematical algorithm utilized for the comparison of sequences is the algorithm of Myers and Miller, CABIOS (1989). The ALIGN program (version 2.0) which is part of the GCG sequence alignment software package has incorporated such an algorithm. Other algorithms for sequence analysis known in the art include ADVANCE and ADAM as described in Torellis and Robotti (1994) Comput. Appl. Biosci., 10:3-5; and FASTA described in Pearson and Lipman (1988) Proc. Natl. Acad. Sci. 85:2444-8. Within FASTA, ktup is a control option that sets the sensitivity and speed of the search.

It is often advantageous to reduce the length of a polypeptide, provided that the resultant reduced length polypeptide still has a desired activity. "Fragment" refers to a peptide or polypeptide comprising an amino acid sequence of at least 5 amino acid residues (preferably, at least 10 amino acid residues, at least 15 amino acid residues, at least 20 amino acid residues, at least 25 amino acid residues, at least 40 amino acid residues, at least 50 amino acid residues, at least 60 amino residues, at least 70 amino acid residues, at least 80 amino acid residues, at least 90 amino acid residues, at least 100 amino acid residues, at least 125 amino acid residues, at least 150 amino acid residues, at least 175 amino acid residues, at least 200 amino acid residues, or at least 250 amino acid residues) of the amino acid sequence of a). The fragment possesses the functional activity of the polypeptide of the invention. Such fragments are encompassed by the present invention.

The polypeptides of the present invention (including homologues and fragments) may be modified either by natural processes, such as processing or other post-translational modifications, or by chemical modification techniques which are well known in the art. Among the numerous known modifications which may be present include, but are not limited to, acetylation, acylation, amidation, ADP-ribosylation, glycosylation, GPI anchor formation, covalent attachment of a lipid or lipid derivative, methylation, myristylation, pegylation, prenylation, phosphorylation, ubiquitination, or any similar process.

The polypeptides of the present invention (including homologues and fragments) may be provided in isolated or recombinant form, and may be fused to other moieties. The polypeptides (including homologues and fragments) may be provided in substantially pure form, that is to say free, to a substantial extent, from other proteins. Thus, a polypeptide may be provided in a composition in which it is the predominant component present (i.e. it is present at a level of at least 50%; preferably at least 75%, at least 90%, or at least 95%; when determined on a weight/weight basis excluding solvents or carriers).

As used herein with respect to polypeptides, "isolated" means separated from its native environment and present in sufficient quantity to permit its identification or use. Isolated, when referring to a protein or polypeptide, means, for example (i) selectively produced by expression cloning or (ii) purified by chromatography or electrophoresis. Isolated polypeptides may, but need not be, substantially pure. The term "substantially pure" means that the polypeptides are essentially free of other substances with which they may be found in nature or in vivo systems to an extent practical and appropriate for their intended use. A "recombinant polypeptide" is a polypeptide isolated, purified, or identified by virtue of expression in a heterologous cell, said cell having been transformed or transfected, either transiently or stably, with a recombinant vector engineered to drive expression of the polypeptide in the host cell.

The polypeptides of the present invention can be coded for by a large variety of nucleic acid molecules, taking into account the well-known degeneracy of the genetic code. All of these molecules are within the scope of the present invention. Thus, the present invention provides a nucleic acid molecule comprising a nucleotide sequence encoding a polypeptide of the invention, as well as a nucleic acid molecule comprising a nucleotide sequence complementary to a nucleotide sequence encoding a polypeptide of the invention.

Nucleic acid molecules of the invention may utilise codons that are used more often in the organism in which the nucleic acid molecule is to be expressed. For example, nucleic acid molecules of the present invention may use yeast-biased or insect-biased codons.

The invention provides a nucleic acid comprising the nucleotide sequence of FIG. 9 (SEQ ID NO: 5). This nucleic acid codes for ΔN1hRD-M protein (M=12-amino acid c-myc tag) as described in WO 2007/129050 synthesised using yeast-biased codons. When co-expressed with a CYP, this nucleic acid yields higher CYP specific activities than that was obtained using the ΔN1hRD-M gene that had been derived from the wt-hRD gene isolated from a human liver cDNA library.

The terms "nucleic acid molecule" and "nucleotide sequence" include double and single stranded DNA and RNA molecules and backbone modifications thereof. The nucleic acid molecule of the present invention may be in isolated, recombinant, non-natural or chemically synthetic form. As used herein with respect to nucleic acid molecules, "isolated or "recombinant" means any of a) amplified in vitro by, for example, polymerase chain reaction (PCR), b) recombinantly produced by cloning, c) purified by, for example, gel separation, and d) synthesised, such as by chemical synthesis. The nucleic acid molecules of the present invention may be synthesised using methods known in the art, such as using conventional chemical approaches or polymerase chain reaction (PCR) amplification.

The present invention includes nucleic acid molecules comprising a sequence complementary to a sequence as defined above. Thus, for example, both strands of a double stranded nucleic acid molecule are included within the scope of the present invention (whether or not they are associated with one another). Also included are mRNA molecules and complementary DNA molecules (e.g. cDNA molecules).

The nucleic acid molecule of the present invention may further comprise a promoter or other regulatory sequence which controls expression of the nucleotide sequence. The promoter may be an inducible promoter, which may be a GAL promoter. The promoter may comprise a truncated GAL promoter. The truncated GAL promoter may be a truncated GAL1 promoter. The truncated GAL1 promoter may be a GAL1 promoter truncated at nucleotide 202 as described in WO2007/129050. Alternatively, the inducible promoter may be an ADH2 promoter.

The nucleic acid molecule of the invention may further comprise a transcription termination sequence, which may be downstream of the promoter. The nucleic acid molecule may comprise unique restriction sites between the GAL promoter and termination sequence that allow insertion of a nucleotide sequence under the control of the promoter. The transcription termination sequence may be immediately downstream of the inserted nucleotide sequence or separated by a minimal distance. The transcription termination sequence may be separated from the inserted nucleotide sequence by 5-25 nucleotides. It may be separated by 5-20, 5-15, 15-20, 5-10, 6-9 or 6-8 nucleotides. It may be separated by 5, 6, 7, 8, 9, 10, 11, 12, 13, 14, 15, 16, 17, 18, 19 or 20 nucleotides. The termination sequence may be a termination sequence from any expressed gene and may be selected from SUC2 (SUC2t), PHO5, ADH1, ADH2 or CYC1.

Nucleic acid molecules of the present invention can be inserted into vectors and cloned to provide large amounts of DNA or RNA for further study. Suitable vectors may be introduced into host cells to enable the expression of polypeptides used in the present invention using techniques known to the person skilled in the art. Thus, the present invention provides a vector comprising a nucleic acid molecule of the present invention. Also provided are isolated cells comprising a nucleic acid or vector of the present invention. Such cells may be eukaryotic. They may be mammalian (such as human), yeast or insect cells.

The term "vector" refers to a nucleic acid molecule having a nucleotide sequence that can assimilate new nucleic acid molecules, and propagate those new sequences in an appropriate host.

The vector may cause expression of the nucleic acid molecule in a target cell. The target cell may be a eukaryotic cell and may be a yeast, mammalian or insect cell. The vector may be an integrating vector. The vector may be capable of integration into the genome of the target cell. The vector may be selected from plasmid vectors, cosmid vectors, phage vectors, episomally replicating vectors, retroviral vectors, lentiviral vectors, adenovirus-associated virus (AAV) vectors, adenoviral vectors and baculovirus vectors. Such vectors are known in the art and any of these may be employed in the present invention. The vector may be a yeast integrating vector.

The vector may comprise one or more expressed markers such as selective markers and/or reporter genes which enable selection of cells transfected (or transformed: the terms are used interchangeably in this text) with them and preferably, to enable a selection of cells containing vectors incorporating heterologous DNA. A suitable start and stop signal will generally be present and if the vector is intended for expression, sufficient regulatory sequences to drive expression will be present.

The vector may allow integration of the nucleic acid molecule at the locus of any specific gene in the genome of the target cell. The vector may be capable of integration into a yeast cell and may be capable if integration into the yeast genome.

The vectors and nucleic acid molecules of the invention may be integrated into the host cell genome by random integration or by homologous recombination. Alternatively, they may be targeted to a specific location in the host cell by methods known in the art such as a site specific recombinase or integrase for integration into a specific site. This may allow the vector and/or nucleic acid molecule to be targeted into a known region with particular characteristics such as being permissive for expression or to avoid integration in a gene of the host cell. The nucleic acid molecules and/or vectors of the present invention may be introduced into cells using a variety of methods known in the art. Where the nucleic acid molecules and/or vectors are introduced into a cell in vitro, conventional techniques such as transfection, liposomes, viruses or lipid reagents may be employed. Electroporation may be used to introduce the nucleic acid molecules and/or vectors into cells, and in particular into mammalian cells.

A further aspect of the invention provides a method of expressing a nucleic acid molecule of the invention in a cell, comprising transforming the cell with a nucleic acid molecule of the invention and/or vector of the invention. A further aspect provides a method of obtaining a polypeptide of the invention, comprising transforming a cell with a nucleic acid molecule of the invention and/or vector of the invention and isolating the expressed protein. In either aspect, the cell may be a eukaryotic cell. The cell may be a yeast cell, insect cell or mammalian cell.

The invention also provides a method of producing a yeast strain expressing a nucleic acid molecule of the invention, comprising transforming a yeast strain with a nucleic acid molecule of the invention and/or with a vector of the invention. Also provided is a yeast strain produced by such a method. The yeast strain may be selected from those known in the art. The yeast strain may be *Saccharomyces cerevisiae* and/or optionally selected from the yeast strains JL20 (Daum, G et al. Yeast Functional Analysis Report, *Yeast*, 15(7), 601-614) and W303B (Furuchi, T et al. *Nucleic Acids Res.* 2004; 32(8): 2578-2585). A yeast strain expressing a nucleic acid molecule of the invention enables the provision of a system for providing increased activity and/or expression of cytochrome P450.

The present invention also provides a protein expression system comprising:
  i) a cell or yeast strain of the invention; and
  ii) a vector comprising a nucleotide sequence encoding a target protein, said sequence being under the control of a promoter which causes expression of the nucleotide sequence.

The target protein may be a cytochrome P450, which may be a heterologous cytochrome P450 and may be human cytochrome P450. Alternatively, the target protein may be a cytochrome b5 protein, which may be a heterologous cytochrome b5 protein. The cytochrome b5 protein may be a human b5 protein. Cytochrome b5 protein is a co-factor that contributes to cytochrome P450 activity. The vector may comprise a nucleotide sequence encoding a cytochrome P450 and a nucleotide sequence encoding a cytochrome b5 protein, the sequences under the control of diverse promoters. The vector may cause expression of the, or each, nucleotide sequence on integration into the cell or yeast genome.

The present invention also provides a method of producing a cytochrome P450 with increased activity and/or increased expression levels, the method comprising:
  (a) transforming a cell of the invention with a vector capable of directing the expression of cytochrome P450, or
  (b) transforming a cell with a nucleic acid of the invention and/or with a vector of the invention and optionally transforming the cell with a nucleic acid molecule comprising a nucleotide sequence encoding a cytochrome P450 and/or a vector which directs expression of the nucleotide sequence encoding the cytochrome P450. The nucleotide sequence may encode heterologous cytochrome P450, which may be human cytochrome P450.

These methods may further comprise transforming the cell with a nucleic acid molecule comprising a nucleotide sequence encoding a cytochrome b5 protein and/or a vector which directs the expression of a nucleotide sequence encoding a cytochrome b5 protein.

Preferred features of each aspect of the invention are as for each of the other aspects mutatis mutandis. The prior art documents mentioned herein are incorporated to the fullest extent permitted by law.

EXAMPLES

The present invention will now be described in more detail with reference to the following non-limiting examples. Reference is made to the accompanying drawings in which:

FIG. 7 is a comparison of the protein sequences of wt-hRD (SEQ ID NO: 6), ΔN1hRD (SEQ ID NO: 7) and ΔN2hRD (SEQ ID NO: 8).

FIG. 8 is a comparison of the protein sequences of wt-hRD (SEQ ID NO: 6), ΔN1hRD-M (SEQ ID NO: 9), ΔN1hRD-HDEL (SEQ ID NO: 3) and ΔN2hRD-HDEL (SEQ ID NO: 4).

FIG. 9 shows the nucleic acid sequence of the BamHI-XbaI DNA fragment of the ΔN1hRD-M gene chemically synthesized using yeast biased codons (SEQ ID NO: 5); the Start Site is at base 12 and indicated in bold.

FIG. 13 is a graph comparing ROS produced by the human ΔN1hRD-M gene (isolated from a human liver cDNA library) and the one synthesized using yeast-biased codons.

FIG. 14 is a graph comparing of ROS produced by three hRD variant genes, synthesized using yeast-biased codons.

EXAMPLE 1—CLONING OF THE 573 BP YEAST ADH2 PROMOTER AS A SALI(NGOMIV)-(HINDIII)BAMHI FRAGMENT IN PBLUESCRIPT

The cloning of a SalI(NgoMIV)-(HindIII)BamHI ADH2 promoter fragment (SEQ ID 1) in pBlueScriptII SK(+) was performed using ADH2 promoter sequence specific primers (5' PCR primer: 5'-CCGGTCGACG CCGGCGGCAA AACGTAGGGG CAAACAAACG G-3' (SEQ ID NO: 10—the first six letters in italics signify the SalI site and the next six letters represent the NgoMIV site) & 3' PCR primer: 5'-CGGGATCCAA GCTTTGTGTA TTACGATATA GTTAATAG-3' (SEQ ID NO: 11—the first six letters in italics signify the BamHI site and the next six letters represent the HindIII site). The amplified fragment, digested with SalI-BamHI, was cloned in pBlueScriptII KS(+) digested with SalI-BamHI.

The ADH2 promoter.
(SEQ ID NO: 12)
```
  1 CCGGTCGACG CCGGCGGCAA AACGTAGGGG CAAACAAACG
    GAAAAATCGT

51 TTCTCAAATT TTCTGATGCC AAGAACTCTA ACCAGTCTTA
    TCTAAAAATT

101 GCCTTATGAT CCGTCTCTCC GGTTACAGCC TGTGTAACTG
    ATTAATCCTG

151 CCTTTCTAAT CACCATTCTA ATGTTTTAAT TAAGGGATTT
    TGTCTTCATT

201 AACGGCTTTC GCTCATAAAA ATGTTATGAC GTTTTGCCCG
    CAGGCGGGAA

251 ACCATCCACT TCACGAGACT GATCTCCTCT GCCGGAACAC
    CGGGCATCTC

301 CAACTTATAA GTTGGAGAAA TAAGAGAATT TCAGATTGAG
    AGAATGAAAA

351 AAAAAAAAAA AAAAAAGGCA GAGGAGAGCA TAGAAATGGG
    GTTCACTTTT

401 TGGTAAAGCT ATAGCATGCC TATCACATAT AAATAGAGTG
    CCAGTAGCGA

451 CTTTTTTCAC ACTCGAAATA CTCTTACTAC TGCTCTCTTG
    TTGTTTTTAT

501 CACTTCTTGT TTCTTCTTGG TAAATAGAAT ATCAAGCTAC
    AAAAAGCATA

551 CAATCAACTA TCAACTATTA ACTATATCGT AATACACAAA
    GCTTGGATCC

601 CG
```

Figure 1:
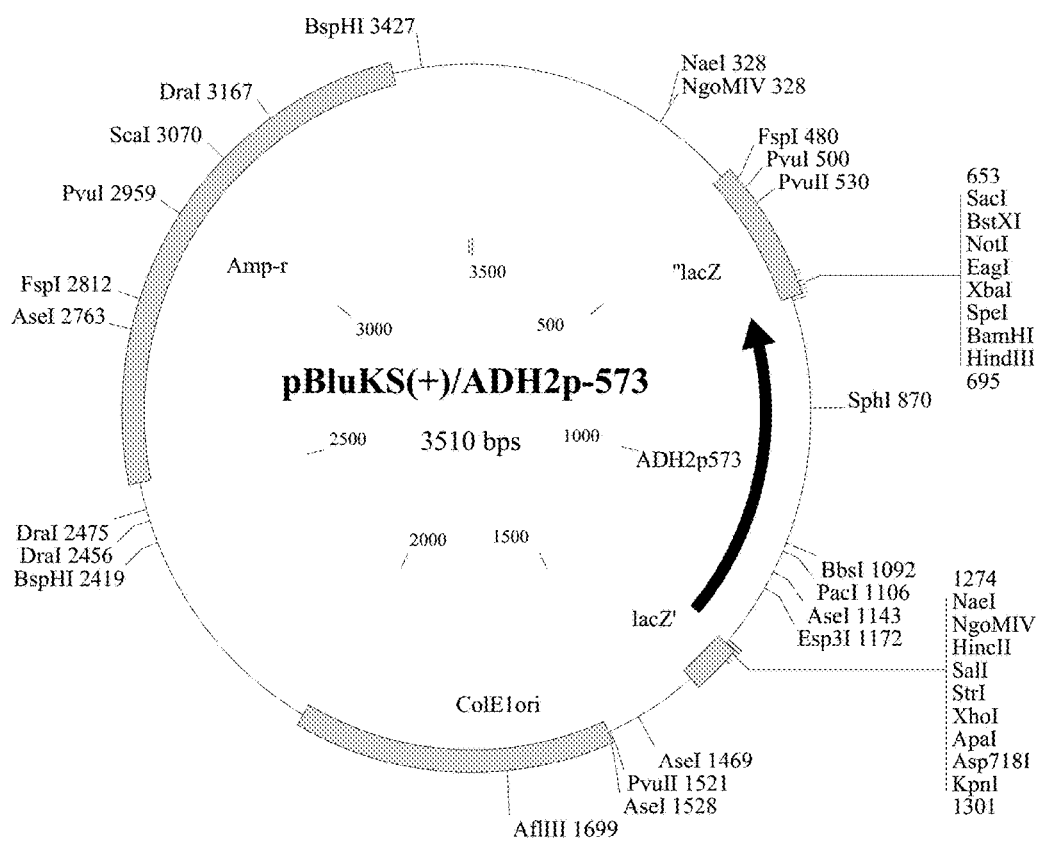
FIG. 1 illustrates the plasmid pBluKS(+)/ADH2p-573.

One correct clone obtained after ligation and transformation in DH5alpha bacterial cells was named pBluKS(+)/ADH2p-573 (FIG. 1) and was used for further cloning in a 2-micron and an integrating yeast expression vector. The veracity of the clone was confirmed by restriction enzyme analysis and corroborated by DNA sequencing.

EXAMPLE 2—CLONING OF THE ADH2 PROMOTER IN A YEAST 2-MICRON VECTOR

Figure 2:
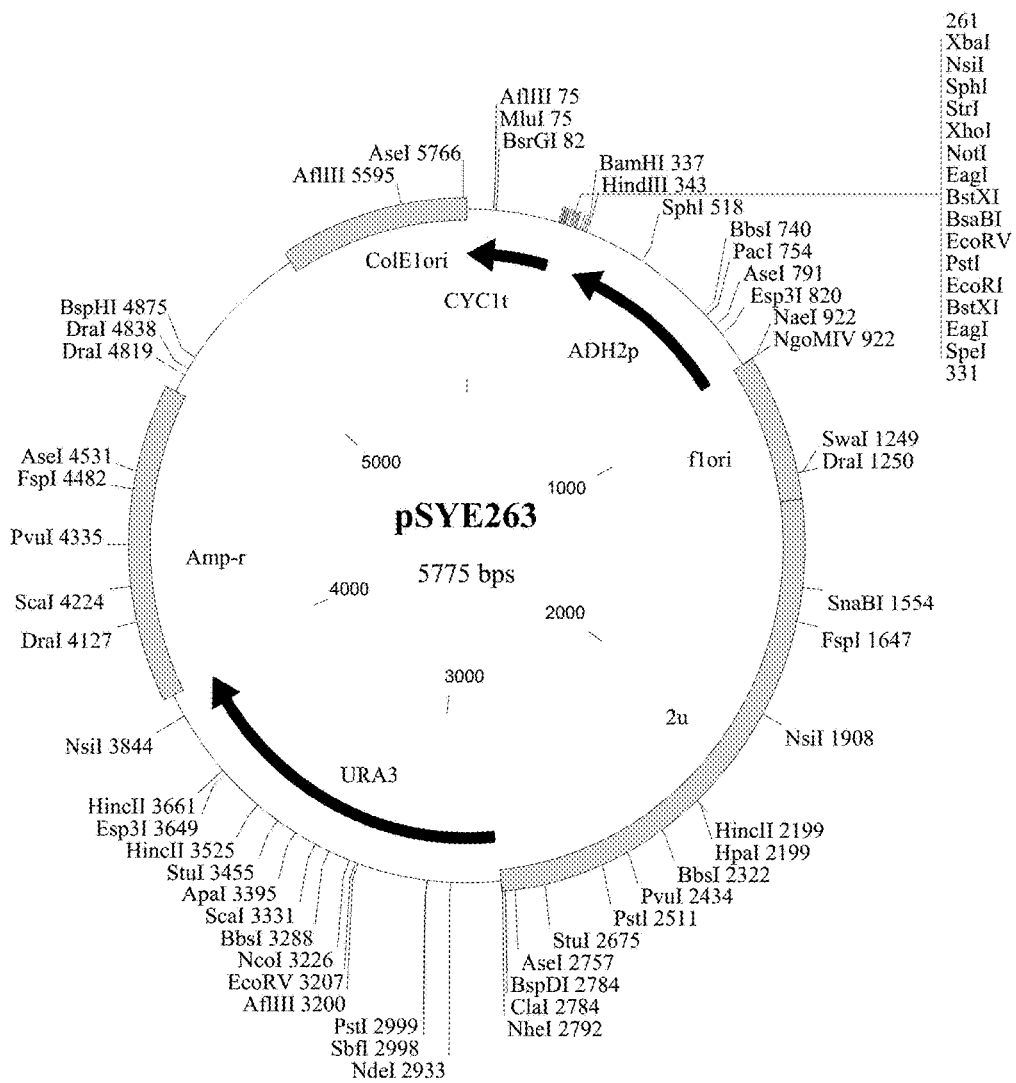
FIG. 2 illustrates the plasmid pSYE263.

A 585 bp NgoMIV-BamHI ADH2 promoter fragment was isolated from pBluKS(+)/ADH2p-573 (FIG. 1) and cloned in pYES2 (a yeast 2-micron vector obtained from Invitrogen) digested with NgoMIV and BamHI to obtain the plasmid pSYE263 (FIG. 2).

EXAMPLE 3—CLONING OF THE HUMAN CYP2D6 GENE IN PSYE263

Figure 3:
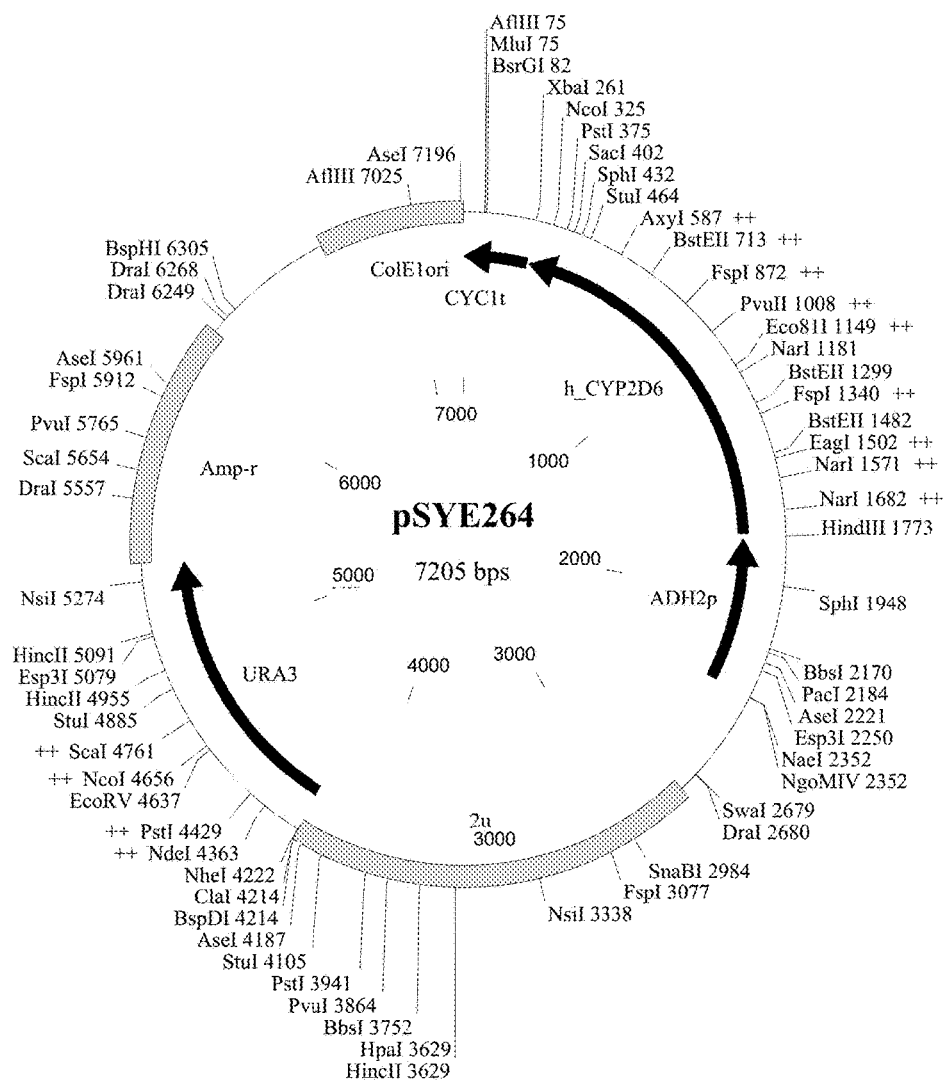
FIG. 3 illustrates the plasmid pSYE264.

A 1506 bp BamHI-XbaI fragment containing the human CYP2D6 gene (SEQ ID No. 2) was cloned in pSYE263 (FIG. 2), digested with BamHI and XbaI, to obtain the plasmid pSYE264 (FIG. 3).

The human CYP2D6 gene (1512 bp) as cloned from a human liver cDNA library (SEQ ID NO: 13):
```
   1 GGATCCAAAA AAATGGGGCT AGAAGCACTG GTGCCCCTGG
     CCGTGATAGT

51 GGCCATCTTC CTGCTCCTGG TGGACCTGAT GCACCGGCGC
     CAACGCTGGG

101 CTGCACGCTA CCCACCAGGC CCCCTGCCAC TGCCCGGGCT
     GGGCAACCTG

151 CTGCATGTGG ACTTCCAGAA CACACCATAC TGCTTCGACC
     AGTTGCGGCG

201 CCGCTTCGGG GACGTGTTCA GCCTGCAGCT GGCCTGGACG
     CCGGTGGTCG

251 TGCTCAATGG GCTGGCGGCC GTGCGCGAGG CGCTGGTGAC
     CCACGGCGAG

301 GACACCGCCG ACCGCCCGCC TGTGCCCATC ACCCAGATCC
     TGGGTTTCGG

351 GCCGCGTTCC CAAGGGGTGT TCCTGGCGCG CTATGGGCCC
     GCGTGGCGCG

401 AGCAGAGGCG CTTCTCCGTG TCCACCTTGC GCAACTTGGG
     CCTGGGCAAG

451 AAGTCGCTGG AGCAGTGGGT GACCGAGGAG GCCGCCTGCC
     TTTGTGCCGC

501 CTTCGCCAAC CACTCCGGAC GCCCCTTTCG CCCCAACGGT
     CTCTTGGACA

551 AAGCCGTGAG CAACGTGATC GCCTCCCTCA CCTGCGGGCG
     CCGCTTCGAG

601 TACGACGACC CTCGCTTCCT CAGGCTGCTG GACCTAGCTC
     AGGAGGGACT

651 GAAGGAGGAG TCGGGCTTTC TGCGCGAGGT GCTGAATGCT
     GTCCCCGTCC

701 TCCTGCATAT CCCAGCGCTG GCTGGCAAGG TCCTACGCTT
     CCAAAAGGCT

751 TTCCTGACCC AGCTGGATGA GCTGCTAACT GAGCACAGGA
     TGACCTGGGA

801 CCCAGCCCAG CCCCCCCGAG ACCTGACTGA GGCCTTCCTG
     GCAGAGATGG

851 AGAAGGCCAA GGGGAACCCT GAGAGCAGCT TCAATGATGA
     GAACCTGCGC

901 ATAGTGGTGG CTGACCTGTT CTCTGCCGGG ATGGTGACCA
     CCTCGACCAC

951 GCTGGCCTGG GGCCTCCTGC TCATGATCCT ACATCCGGAT
     GTGCAGCGCC

1001 GTGTCCAACA GGAGATCGAC GACGTGATAG GGCAGGTGCG
     GCGACCAGAG

1051 ATGGGTGACC AGGCTCACAT GCCCTACACC ACTGCCGTGA
     TTCATGAGGT

1101 GCAGCGCTTT GGGGACATCG TCCCCCTGGG TATGACCCAT
     ATGACATCCC

1151 GTGACATCGA AGTACAGGGC TTCCGCATCC CTAAGGGAAC
     GACACTCATC

1201 ACCAACCTGT CATCGGTGCT GAAGGATGAG GCCGTCTGGG
     AGAAGCCCTT

1251 CCGCTTCCAC CCCGAACACT TCCTGGATGC CAGGGCCAC
     TTTGTGAAGC

1301 CGGAGGCCTT CCTGCCTTTC TCAGCAGGCC GCCGTGCATG
     CCTCGGGGAG

1351 CCCCTGGCCC GCATGGAGCT CTTCCTCTTC TTCACCTCCC
     TGCTGCAGCA
```

```
1401 CTTCAGCTTC TCGGTGCCCA CTGGACAGCC CCGGCCCAGC
     CACCATGGTG

1451 TCTTTGCTTT CCTGGTGAGC CCATCCCCCT ATGAGCTTTG
     TGCTGTGCCC

1501 CGCTAGTCTA GA
```

EXAMPLE 4—CLONING OF THE HUMAN CYP1A2 GENE IN PSYE263

Figure 4:
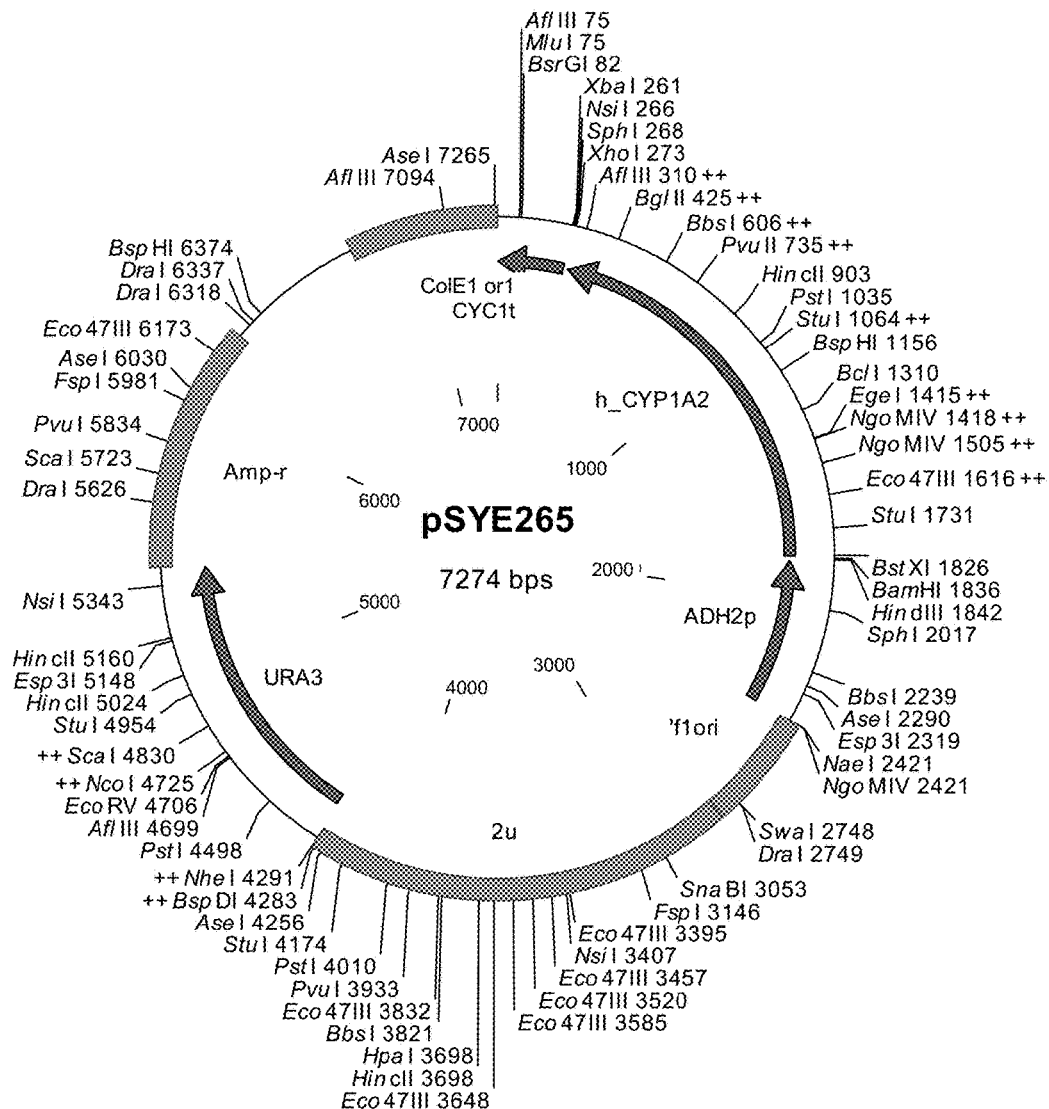
FIG. 4 illustrates the plasmid pSYE265.

A 1563 bp BamHI-XhoI fragment containing the human CYP1A2 gene (SEQ ID No. 12) was cloned in pSYE263 (FIG. 2), digested with BamHI and XhoI, to obtain the plasmid pSYE265 (FIG. 4).

```
The human CYP1A2 gene (1573 bp) as cloned from a
human liver cDNA library (SEQ ID NO: 14).
   1 ATGGATCCAA AAAAATGGCA TTGTCCCAGT CTGTTCCCTT
     CTCGGCCACA

51 GAGCTTCTCC TGGCCTCTGC CATCTTCTGC CTGGTATTCT
     GGGTGCTCAA

101 GGGTTTGAGG CCTCGGGTCC CCAAAGGCCT GAAAAGTCCA
     CCAGAGCCAT

151 GGGGCTGGCC CTTGCTCGGG CATGTGCTGA CCCTGGGGAA
     GAACCCGCAC

201 CTGGCACTGT CAAGGATGAG CCAGCGCTAC GGGGACGTCC
     TGCAGATCCG

251 CATTGGCTCC ACGCCCGTGC TGGTGCTGAG CCGCCTGGAC
     ACCATCCGGC

301 AGGCCCTGGT GCGGCAGGGC GACGATTTCA AGGGCCGGCC
     TGACCTCTAC

351 ACCTCCACCC TCATCACTGA TGGCCAGAGC TTGACCTTCA
     GCACAGACTC

401 TGGACCGGTG TGGGCTGCCC GCCGGCGCCT GGCCCAGAAT
     GCCCTCAACA

451 CCTTCTCCAT CGCCTCTGAC CCAGCTTCCT CATCCTCCTG
     CTACCTGGAG

501 GAGCATGTGA GCAAGGAGGC TAAGGCCCTG ATCAGCAGGT
     TGCAGGAGCT

551 GATGGCAGGG CCTGGGCACT TCGACCCTTA CAATCAGGTG
     GTGGTGTCAG

601 TGGCCAACGT CATTGGTGCC ATGTGCTTCG GACAGCACTT
     CCCTGAGAGT

651 AGCGATGAGA TGCTCAGCCT CGTGAAGAAC ACTCATGAGT
     TCGTGGAGAC

701 TGCCTCCTCC GGGAACCCCC TGGACTTCTT CCCCATCCTT
     CGCTACCTGC

751 CTAACCCTGC CCTGCAGAGG TTCAAGGCCT TCAACCAGAG
     GTTCCTGTGG

801 TTCCTGCAGA AACAGTCCA GGAGCACTAT CAGGACTTTG
     ACAAGAACAG

851 TGTCCGGGAC ATCACGGGTG CCCTGTTCAA GCACAGCAAG
     AAGGGGCCTA

901 GAGCCAGCGG CAACCTCATC CCACAGGAGA AGATTGTCAA
     CCTTGTCAAT

951 GACATCTTTG GAGCAGGATT TGACACAGTC ACCACAGCCA
     TCTCCTGGAG
```

```
1001 CCTCATGTAC CTTGTGACCA AGCCTGAGAT ACAGAGGAAG
     ATCCAGAAGG

1051 AGCTGGACAC TGTGATTGGC AGGGAGCGGC GGCCCCGGCT
     CTCTGACAGA

1101 CCCCAGCTGC CCTACTTGGA GGCCTTCATC CTGGAGACCT
     TCCGACACTC

1151 CTCCTTCTTG CCCTTCACCA TCCCCCACAG CACAACAAGG
     GACACAACGC

1201 TGAATGGCTT CTACATCCCC AAGAAATGCT GTGTCTTCGT
     AAACCAGTGG

1251 CAGGTCAACC ATGACCCAGA GCTGTGGGAG GACCCCTCTG
     AGTTCCGGCC

1301 TGAGCGGTTC CTCACCGCCG ATGGCACTGC CATTAACAAG
     CCCTTGAGTG

1351 AGAAGATGAT GCTGTTTGGC ATGGGCAAGC GCCGGTGTAT
     CGGGGAAGTC

1401 CTGGCCAAGT GGGAGATCTT CCTCTTCCTG GCCATCCTGC
     TACAGCAACT

1451 GGAGTTCAGC GTGCCGCCGG GCGTGAAAGT CGACCTGACC
     CCCATCTACG

1501 GGCTGACCAT GAAGCACGCC CGCTGTGAAC ATGTCCAGGC
     GCGGCTGCGC

1551 TTCTCCATCA ACTGACTCGA GAT
```

EXAMPLE 5—CLONING OF THE ADH2 PROMOTER IN A YEAST INTEGRATING VECTOR

Figure 5:
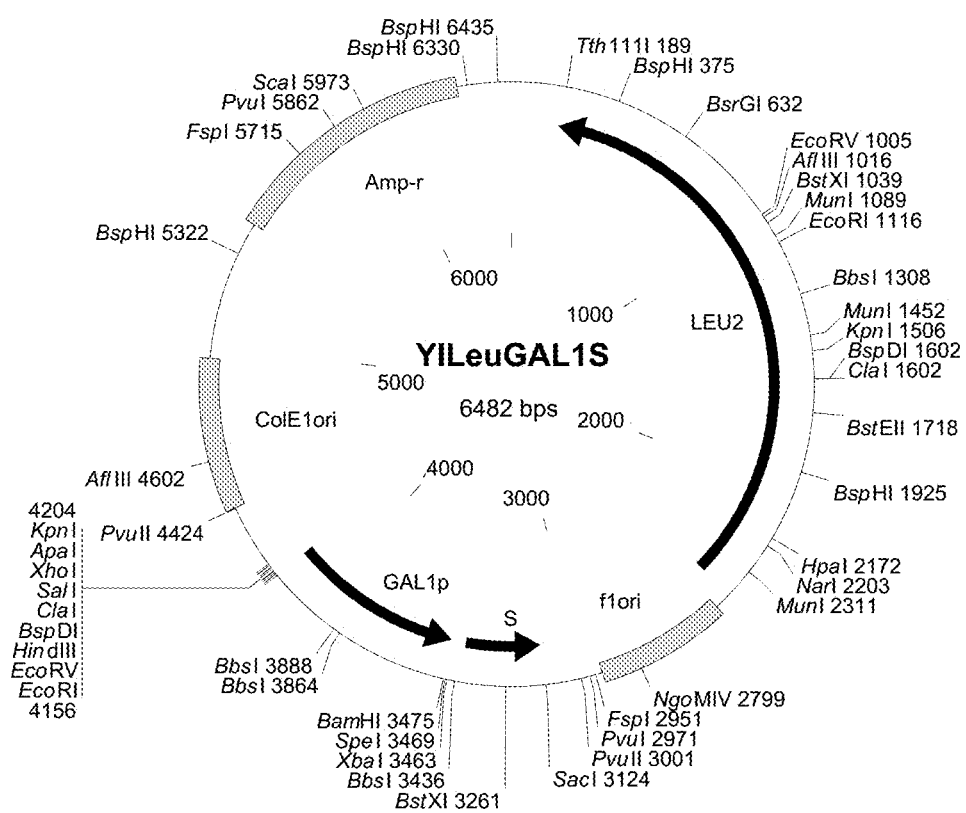
FIG. 5 illustrates the basic yeast integrating plasmid YILEUGAL1S.
Figure 6:
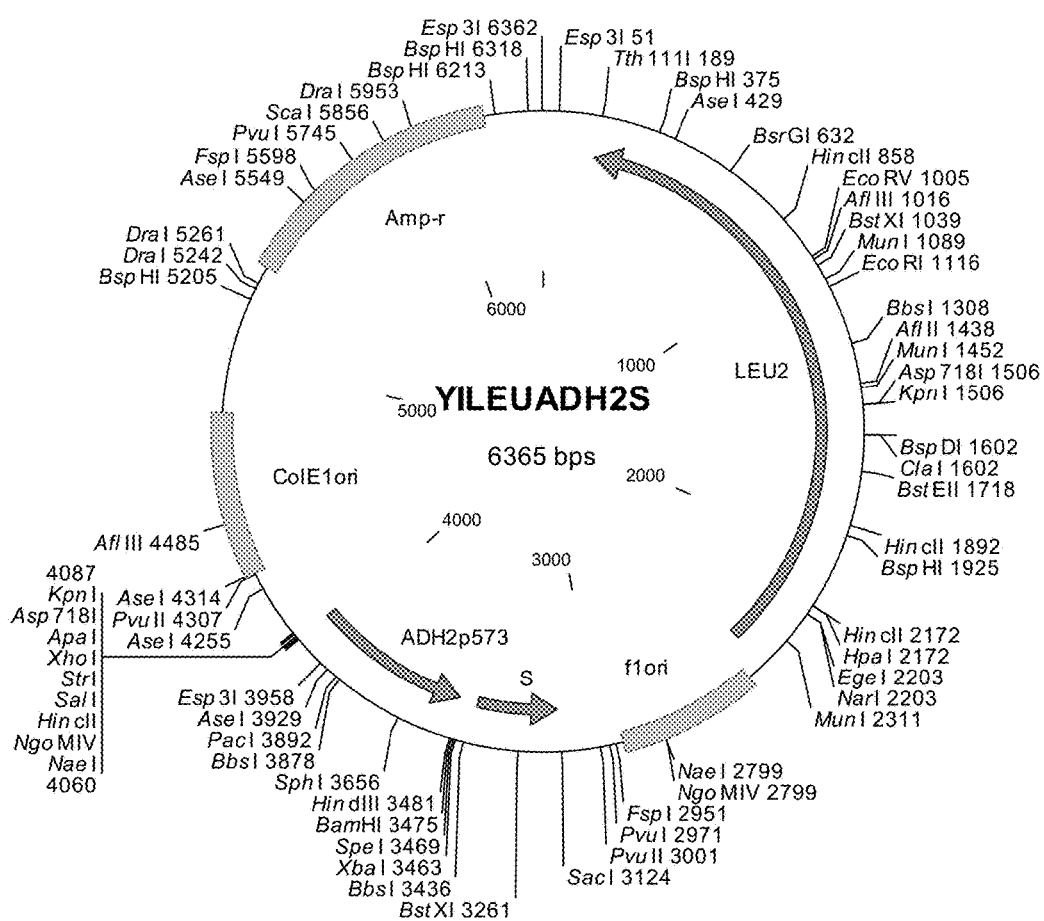
FIG. 6 illustrates the plasmid YILEUADH2S.

A 591 bp SalI-BamHI ADH2 promoter fragment was isolated from pBluKS(+)/ADH2p-573 (FIG. 1) and cloned in YILEUGAL1 S (FIG. 5; a yeast LEU2-integrating vector created in-house) digested with SalI and BamHI to obtain the plasmid YILEUADH2S (FIG. 6). 'S' signifies the SUC2 gene terminator.

EXAMPLE 6—CONSTRUCTION OF THE HRD VARIANT GENES

Different variants of the hRD gene were constructed to obtain hRD activity that may not be deleterious for P450 expression. The aim was to devise an optimal system that allows better production of human P450 isozymes in yeast. The ultimate goal was to find an alternative system for the production of recombinant human P450 isozymes not only in yeast but also in insect and mammalian cells.

For yeast expression, the first variant gene of the human P450 reductase was constructed via chemical synthesis of the gene using yeast-biased codons. The other two variants were constructed from the first via PCR using sequence specific primers.

The first variant lacks the negatively charged (5 negatively charged amino acids+a potential positively charged amino acid) N-terminal 24 amino acids and the COOH-terminal Stop codon (FIG. 7; ΔN1hRD—SEQ ID NO: 7) but contains the c-myc epitope tag EQKLISEEDLNG (SEQ ID NO: 15) at the COOH-terminal end (FIG. 8; ΔN1hRD-M—SEQ ID NO: 9). The 12 amino acid c-myc tag is also a negatively charged peptide (containing 4 negatively charged amino acids and a positively charged amino acid) and is linked to the C-terminus of hRD. The c-myc tag also allows monitoring of P450 reductase protein production inside the cell. This variant is referred to as ΔN1hRD-M (SEQ ID NO: 9).

The second variant also lacks the negatively charged N-terminal 24 amino acids and the COOH-terminal Stop codon (FIG. 7; ΔN1hRD—SEQ ID NO: 7) but contains a 4-amino acid yeast endoplasmic reticular retention signal, HDEL (SEQ ID NO: 1) (FIG. 8; ΔN1hRD-HDEL—SEQ ID NO: 3). The DNA sequence was constructed via using a 3'-primer that codes for the HDEL sequence. This variant has been named ΔN1hRD-HDEL.

The third variant lacks the 54-amino acid membrane anchoring region of human P450 reductase (hRD) and the COOH-terminal Stop codon (FIG. 7) but contains a 4-amino acid yeast endoplasmic reticular retention signal, HDEL (SEQ ID NO: 2) (FIG. 8; ΔN2hRD-HDEL—SEQ ID NO: 4). The DNA sequence was constructed via PCR using a 5'-primer that allows deletion of another 30 amino acids from that 3'-primer that codes for the HDEL sequence. This variant has been named ΔN2hRD-HDEL.

EXAMPLE 7—CONSTRUCTION OF YEAST INTEGRATING PLASMIDS THAT BEAR VARIANTS OF THE HUMAN P450 REDUCTASE (HRD) GENE UNDER THE CONTROL OF THE 573 BP ADH2 PROMOTER

Figure 10:
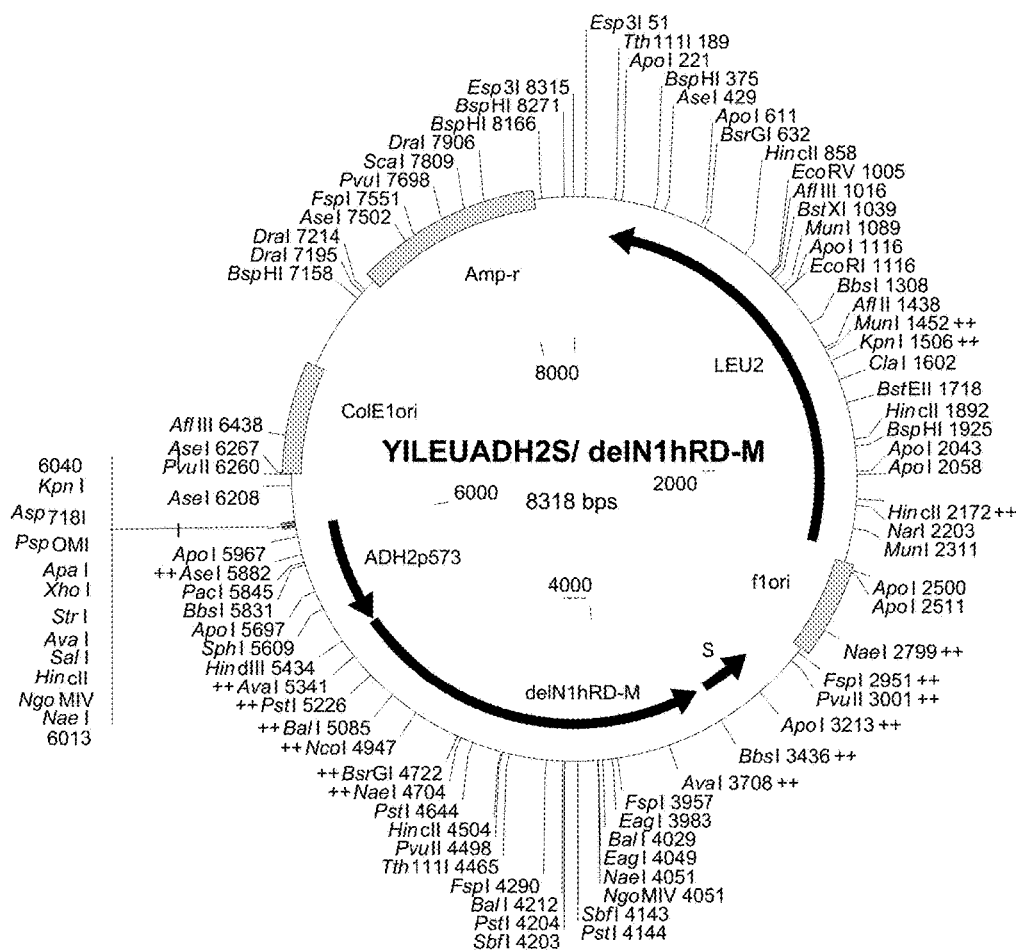
FIG. 10 illustrates the integrating plasmid, YILEUADH2S, that bears the ΔN1hRD-M gene.
Figure 11:
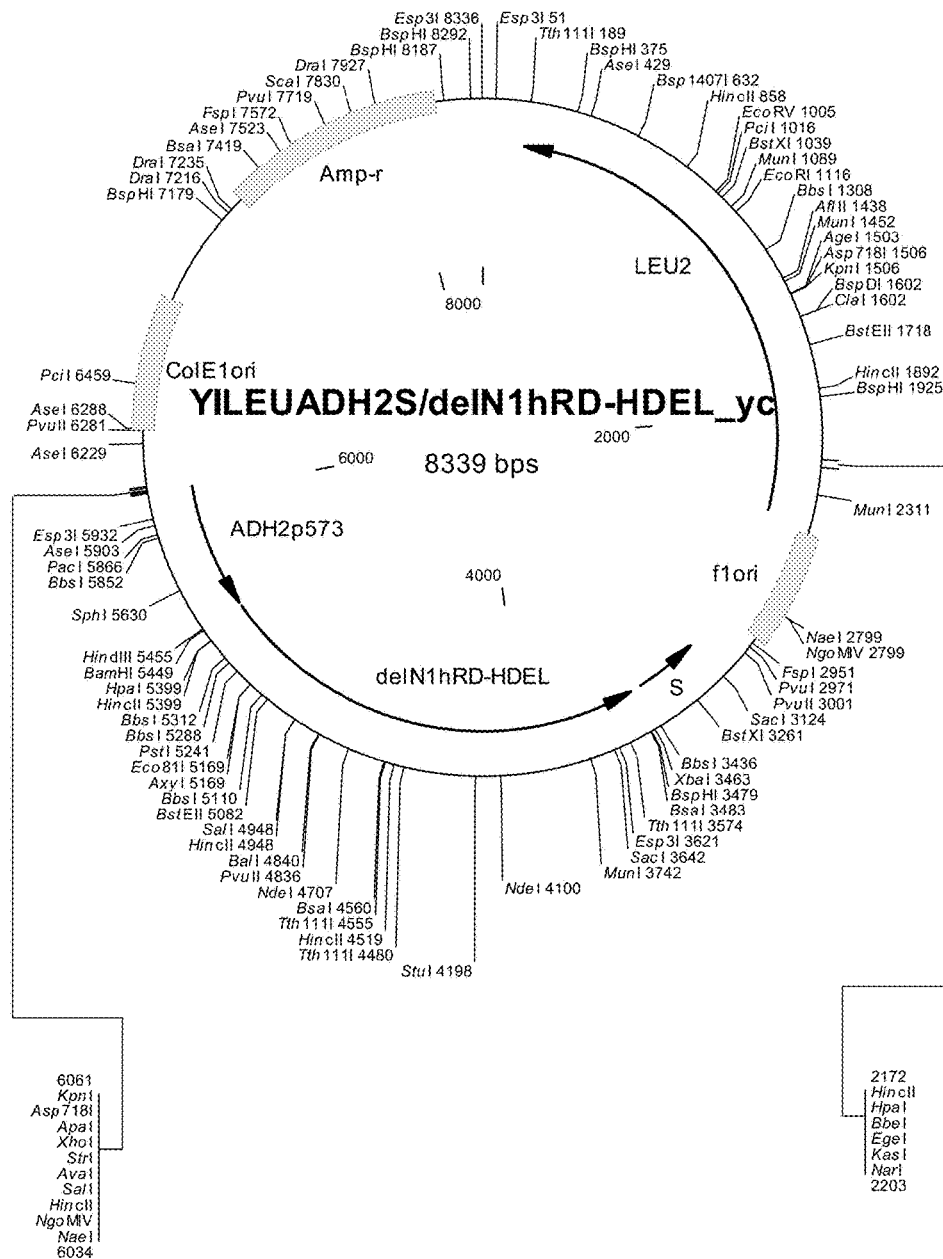
FIG. 11 illustrates the integrating plasmid that bears the ΔN1hRD-HDEL gene in YILEUADH2S.
Figure 12:
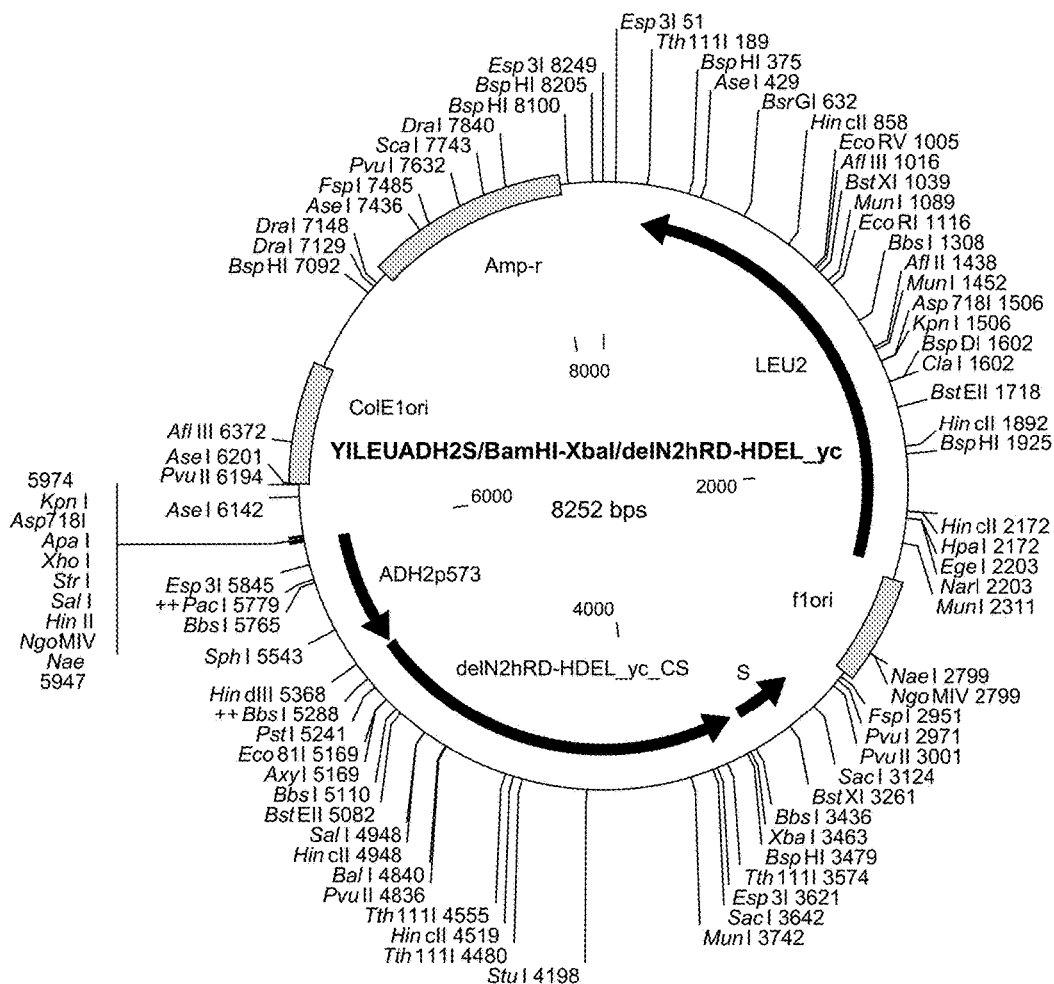
FIG. 12 illustrates the integrating plasmid that bears the ΔN2hRD-HDEL gene in YILEUADH2S.

The hRD variants and the full-length hRD gene were cloned in the yeast integrating vector that would allow expression of hRD under the control of the ADH2 promoter (YILEUADH2MS; FIG. 6). The steps involved were:
(1) Cloning of the hRD variants from a human liver cDNA library in pBlueScript vectors and confirming the inserts via restriction enzyme analysis and DNA sequencing.
(2) Sub-cloning the hRD variant gene, ΔN1hRD-M, chemically synthesized using yeast biased codons and confirmed by DNA sequencing FIG. 9), in a yeast integrating vector that contains the 573 bp ADH2 promoter-SUCt (ADH2-573 promoter+SUC2t) cassette. The hRD gene variant is cloned downstream of the ADH2-573 promoter and upstream of the SUC2 terminator to obtain the plasmid YILEUADH2S/ΔN1hRD-M (FIG. 10).
(3) Constructing via PCR and unique primers the hRD variant genes, ΔN1hRD-HDEL and ΔN2hRD-HDEL, from the ΔN1hRD-M clone which had been synthesised using yeast biased codons.
(4) Sub-cloning the hRD variant genes, ΔN1hRD-HDEL and ΔN2hRD-HDEL, using yeast biased codons, in a yeast integrating vector that contains the 573 bp ADH2 promoter-SUCt (ADH2-573 promoter+SUC2t) cassette. The hRD gene variants are cloned downstream of the ADH2-573 promoter and upstream of the SUC2 terminator to obtain the plasmids YILEUADH2S/ΔN1hRD-HDEL and YILEUADH2S/ΔN2hRD-HDEL (FIGS. 11 and 12).

EXAMPLE 8—EXPRESSION OF HUMAN CYP GENES IN YEAST

The hRD variant genes, (ΔN1hRD-M, ΔN1hRD-HDEL, ΔN2hRD-HDEL), were integrated into *Saccharomyces cerevisiae* strain W303B (MAT a leu2 his3 trp1 can1-100 ade2 trp1 ura3) using standard yeast transformation procedures as detailed below. The integrating plasmids, bearing the ΔN1hRD-M, ΔN1hRD-HDEL, ΔN2hRD-HDEL genes, were first linearised with the restriction enzyme BstEII before introducing linearised DNA into yeast cells via homologous recombination. The resultant strains were named:
a) W303B-ΔN1hRD-M,
b) W303B-ΔN1hRD-HDEL,
c) W303B-ΔN2hRD-HDEL.

They were used for the transformation of the yeast episomal plasmids that bear the CYP2D6 and CYP1A2 genes:
1. pSYE264 (bearing the human CYP2D6 gene),
2. pSYE265 (bearing the human CYP1A2 gene).

Yeast Transformation

A single colony from the strains W303B-ΔN1hRD-M, W303B-ΔN1hRD-HDEL, W303B-ΔN2hRD-HDEL were picked up from a minimal medium (SD) plate (supplemented with appropriate nutrients depending on the auxotrophic markers in the yeast strain) and inoculated into 10 ml of YPD medium (2% Bacto Peptone, 1% yeast extract, 2% glucose). The cells were grown overnight at 30° C. with 220 rpm shaking. 1.5 ml of overnight cultures were centrifuged at 13,000 rpm for a few seconds to collect the cell pellets. 0.5-2 μg of transforming DNA (i.e. the CYP bearing expression plasmids, pSYE264 and pSYE265) and 100 μg of single-stranded salmon sperm DNA were added to pellets and vortexed briefly. 500 μl of PEG solution (40% PEG 3350, 0.1M lithium acetate pH 7.5, 10 mM Tris-HCl pH 7.5, 1 mM EDTA pH7.5) and 5-10% DMSO were added to transformation mixes. All mixes were incubated in a Thermo-mixer for 15 min at 25° C. with shaking at 400 rpm, and then were heat shocked for 15 min at 42° C. After 10 min, 5-10% ethanol was added. The cells were pelleted at 8000 rpm for 1 min and were washed twice in 1×TE buffer and re-suspended in 250 μl-500 μl 1×TE pH7.5. The cells were plated out on SD agar medium and incubated at 30° C. for 2-3 days.

The transformants were named:
1. W303B-ΔN1hRD-M:pSYE264,
2. W303B-ΔN1hRD-M:pSYE265,
3. W303B-ΔN1hRD-HDEL:pSYE264,
4. W303B-ΔN1hRD-HDEL:pSYE265,
5. W303B-ΔN2hRD-HDEL:pSYE264,
6. W303B-ΔN2hRD-HDEL:pSYE265.

Yeast Cultures for Microsome Preparation

Recombinant yeast cells were grown in culture using the following protocol:
1. On day one, a loopful of fresh yeast cells from an SD-agar plate was inoculated in 20 ml of SD media (1.34 g/200 ml of yeast nitrogen base) containing required nutrients, 2% glucose, and 0.02% casein enzymatic hydrolysate (casamino acids, Sigma, C-7585; containing all the twenty essential amino acids). The cultures were grown overnight at 30° C. with shaking at 220 rpm.
2. On day two, once $OD_{600}$ (i.e. OD measured at 600 nm) of the cultures reached 5 to 6 OD-s, the cultures were inoculated into 400 ml YPD medium (1% Bacto Peptone, 1% yeast extract, 2% glucose) with appropriate nutrients in 2-liter flask. The YPD cell culture was incubated at 30° C. at 220 rpm for 16 hours.
3. On day three, after 16 hours, optical density was again measured at 600 nm after diluting the original culture 1:10. Once an optical density of the YPD media cell culture reached between 14 and 21 $OD_{600}$, the culture was kept at 4° C.
4. Day 3 continued: a centrifuge was pre-chilled to 4° C. The cell culture grown in YPD broth was transferred into a sterile bucket and was centrifuged at 3622 rpm for 15 minutes. A pellet formed at the bottom of the bucket and the supernatant was poured away. 150 ml of Harvest Buffer (118.2 g of 0.65 M Sorbitol, 10 ml of 1 M Tris-HCl, pH 7.5, 200 µl of 0.5 M EDTA, pH 8.0 made up to a liter) was added; the pellet was gently re-suspended and then centrifuged at 3622 rpm for 15 minutes. At the final step, supernatant was poured away and the dry pellet was frozen at −80° C. and the pellet weight was recorded. The pellets can be kept at −80° C. for any length of time before beginning the microsome preparations.

Microsome Preparation

Microsome preparation is the process where the yeast cells are broken down and differentially centrifuged so that the unbroken cells, nuclei, mitochondria and other cell debris are sedimented out and the endoplasmic reticulum (ER) containing cytochrome P450s are obtained in the supernatant. Unwanted soluble matter is later separated from the ER by further centrifugation or PEG precipitation. The colour of the supernatant is reddish brown due to the presence of haeme, an iron-containing co-factor. The following steps in the procedure outline the method by which microsomes expressing a reductase (wild type or variant) or a CYP enzyme (co-expressed with a variant reductase) were obtained.

The cell pellet that had been obtained from the earlier cell culture was weighed and the weight of cell pellet was recorded. The pellet was gently re-suspended in Harvest Buffer containing 100 mM dithiothreitol (DTT) and 100 mM 4-(2-aminoethyl) benzene sulphonylflouride HCl (AEBSF). 1 g of cell pellet was re-suspended in 1.4 ml of Harvest Buffer containing a general protease inhibitor (i.e. 100 ml of Harvest Buffer+0.266 ml DTT (100 mM)+2.66 ml AEBSF (100 mM)). The cell suspension was cooled to 4° C. Cells were subjected to disruption using a cell disrupter (Constant Systems), pressure was maintained at 22.5 KPSI with a single shot disrupter head. The disrupted cells were centrifuged for 15 minutes at 4500 rpm at 4° C. The volume of supernatant was multiplied by 3.75 to give the volume of DMB TES buffer (10 ml of Tris-HCl (1 M) pH 8.0, 400 µl of EDTA 0.5 M pH 8.0, 30 ml of 4 M sorbitol, made up to 200 ml) that were used. This volume was divided by 40 to give the volume of NaCl, and NaCl volume was divided by 10 to give the volume of PEG solution that were used. A 50% PEG3350 solution was added drop-wise to the supernatant and then put through three high-speed centrifugations and the suspension was mixed gently. The concentrated suspension mixture was then left in the cold room on ice for 20 minutes after which it was centrifuged using the JL10 rotor at 9333 rpm for 20 minutes. The microsome pellet was obtained at the bottom of the bucket and the pellet was then washed with Harvest Buffer twice to remove the remaining 50% PEG3350 solution. Then gently, with the help of a spatula, the pellet was removed and transferred to a homogenizer tube and approximately 5 ml of DMB B buffer (1 ml of 1 M Tris-HCl pH 7.5, final concentration 10 mM, 200 µl of 0.5 M EDTA pH 8.0, final concentration 1.0 mM, 40 ml 20% Glycerol, made up to 100 ml) was added. Microsomes were homogenised gently and then aliquoted in to eppendorf tubes so that the aliquots could be stored at −80° C.

Determination of Total Microsomal Protein Concentrations

Protein concentrations in all microsomal samples were measured using the Bio-Rad Bradford protein estimation kit. The Bradford dye (consisting of Coomassie Brilliant Blue G-250 dye) when mixed with a protein sample changes colour from brown to blue and the colour change is proportional to the amount of protein present in the sample. The intensity of the colour is then compared to the colour seen in protein solutions obtained through serial dilutions of a stock solution of a standard protein, bovine serum albumin (BSA). Each dilution of BSA has a defined protein concentration. Comparison with the BSA standard curve allows determination of the concentration of proteins present in any microsomal sample. For measurements of intensity of the blue colour, absorbance is measured at a wavelength of 595 nm using 96-well flat-bottomed microtitre plates and a Bio-Tek Synergy HT plate reader.

Measurement of total protein concentrations allowed determination of the amount of P450 in a specific amount of total protein. This was essential for standardization of P450 enzymatic assays.

Determination of P450 Amounts Via CO-Difference Spectra

Difference spectra of microsomal preparations were measured in a dual-beam spectrophotometer (Shimadzu) using plastic disposable cuvettes. 850 µl of a solution containing 100 mM potassium phosphate and 20% glycerol (pH7.5) was added to the cuvette, and left for one minute. Then a 'few grains' of sodium hydrosulfite was added, mixed gently to prevent any bubble forming in the cuvette and left for another minute. 150 µl of microsomes were added into the cuvette and the whole suspension was mixed gently. Two cuvettes (one containing sodium hydrosulphite without microsome and the other with microsome) were prepared and a baseline of light absorption of the buffer and microsome mixture was recorded in the dual-beam spectrophotometer from 400 nm to 500 nm. Carbon monoxide was bubbled slowly into one sample cuvette for about one minute, 1 bubble/second. Light absorption was recorded again from 400 nm to 500 nm. The concentration of cytochrome P450 in the cuvette was calculated from the absorption change at 450 nm relative to the absorbance change at 490 nm, using the formula below:

$$P450 \text{ content (nmole/ml)} = (A_{450} - A_{490}) \times df \times 1000/\text{extinction coefficient 450 nm}$$

$$P450 \text{ concentration (nmole/mg protein)} = P450 \text{ content/total protein}$$

$$df = \text{dilution factor(total volume in cuvutte/volume microsome)}$$

$$\text{Extinction Coefficient 420 nm} = 110 \text{ mM}^{-1} \text{ cm}^{-1}$$

$$\text{Extinction Coefficient 450 nm} = 91 \text{ mM}^{-1} \text{ cm}^{-1}$$

Extinction coefficient is the fraction of light lost to scattering and absorption per unit distance in a participating medium. It is the sum of absorption coefficient and scattering coefficient.

Results

The relative amounts of P450 obtained using the different P450 reductase variants (hRD, ΔN1hRD-M, ΔN1hRD-HDEL, ΔN2hRD-HDEL) are shown below in Table 1 and Table 2.

TABLE 1

The relative amounts of CYP2D6 obtained using the P450 reductase variants, hRD, ΔN1hRD-M, ΔN1hRD-HDEL and ΔN2hRD-HDEL (genes synthesized using yeast biased codons).

| Human P450 Reductase Variant | Relative Amounts of CYP2D6 Obtained |
| --- | --- |
| hRD (SEQ ID NO: 6) | 1 |
| ΔN1hRD-M (SEQ ID NO: 9) | 3 ± 10% |
| ΔN1hRD-HDEL (SEQ ID NO: 3) | 3.8 ± 10% |
| ΔN2hRD-HDEL (SEQ ID NO: 4) | 4.0 ± 10% |

TABLE 2

The relative amounts of CYP1A2 obtained using the P450 reductase variants, hRD, ΔN1hRD-M, ΔN1hRD-HDEL and ΔN2hRD-HDEL.

| Human P450 Reductase Variant | Relative Amounts of CYP1A2 Obtained |
| --- | --- |
| hRD (SEQ ID NO: 6) | 1 |
| ΔN1hRD-M (SEQ ID NO: 9) | 3.2 ± 10% |
| ΔN1hRD-HDEL (SEQ ID NO: 3) | 4.0 ± 10% |
| ΔN2hRD-HDEL (SEQ ID NO: 3) | 4.5 ± 10% |

Conclusion

The relative amounts of CYP2D6 and CYP1A2 produced using the mutant human P450 reductases are appreciably higher than that obtained with the wild-type reductase, hRD.

EXAMPLE 9—DIHYDROETHIDIUM ASSAY FOR ROS DETECTION

The reactive oxygen species generated in yeast cells due to expression of a P450 reductase were assessed using dihydroethidium fluorescence assay. Reactive oxygen species reacts with dihydroethidium to produce ethidium bromide which binds to the nuclear DNA and emits red fluorescence. Dihydroethidine is one of the best reagents available for measuring intracellular production of reactive oxygen species. After overnight induction of a P450 reductase, the cultures were analysed for induction of reactive oxygen species. The control (wt-hRD) and test (ΔN1hRD-M, ΔN1hRD-HDEL, ΔN2hRD-HDEL) yeast cultures were washed in sterile PBS and then incubated with dihydroethidium (5 μM final concentration) for 30 min. After washing with sterile PBS twice (to remove the extracellular dye), the samples were transferred into 96-well black plates with transparent bottom (COSTAR®). Fluorescence was measured using a BIO-TEK® plate reader. Excitation and emission wavelengths were 260 and 610 nm respectively. The percent induction in the formation of reactive oxygen species was calculated by comparing with cultures where genes were not induced.

The results are shown in FIG. 13 and FIG. 14. The mutant human P450 reductase, ΔN1hRD-M gene, synthesized using yeast-biased codons produces far less ROS than the ΔN1hRD-M gene that was isolated from the human liver cDNA library. The three mutant human P450 reductases produce far less ROS than the wild-type enzyme, hRD.

EXAMPLE 10—MTT-BASED CYTOCHROME P450 REDUCTASE ASSAY

The enzyme NADPH-cytochrome P450 reductase mediates the transfer of electrons from NADPH to cytochrome P450, other microsomal proteins and cytochrome c. It also catalyses the reduction of many drugs and other compounds such as potassium ferricyanide, 2,6-dichloroindopheonl, 1,1-diphenyl-2-picrylhydrazyl (DPPH), and mitomycin c. Tetrazolium salts are used extensively in cell proliferation and cytotoxicity assays, enzyme assays, histochemical procedures and bacteriological screening. In each of these processes, terazolium salts are metabolically reduced to highly coloured end products called formazans. The compound 3-(4,5-dimethylthiazol-2-yl)-2,5-diphenyltetrazolium bromide (MTT) is a monotetrazolium salt. The reduction of MTT is one of the most frequently used methods for measuring cell proliferation and cytotoxicity. Reduction of MTT by P450 reductase has been assessed as a method for monitoring yeast produced recombinant P450 reductase activity and the protocol was developed on the procedure published by Yim S-K, et al (Yim S-K., Y. C.-H. Ahn T., Hung H-C and Pan J-G. A continuous Spectrophotometric assay for NADPH-cytochrome P450 reductase activity using 3-(4,5 Dimethylthiazol-2-yl)-2,5-diphenyltetrazolium Bromide. *Journal of Biology and Molecular Biology* 38: 366-369, 2005). The principal advantage of this substance is that the reduction of MTT can be assayed directly in the reaction medium by a continuous spectrophotometirc method. The electrons released from NADPH by P450 reductase are transferred to MTT, and then the amounts of reduced MTT is assessed spectrophotometrically by measuring the increase in A610 values that is due to the formation of blue formazan. The extinction coefficient of MTT is 11.3 $mM^{-1}$ $cm^{-1}$. This method offers the advantages of short analysis time with the use of a relatively cheap commercial substrate. The classical assay uses recombinant cytochrome c as a substrate.

Solutions Used for the MTT Assay
- 10 mM potassium phosphate buffer: pH7.4: 8 ml of 1M $K_2HPO_4$ and 2 ml of 1M $KH_2PO_4$ add $ddH_2O$ to make up to 1 liter.
- 10 mM MTT: 41.4 mg of MTT (Sigma, Cat No. M2128) into 10 ml of 10 mM potassium phosphate pH7.4 to give 10 mM MTT.
- 100 mM potassium phosphate buffer: pH7.6: 86.6 ml of 1M $K_2HPO_4$ and 13.4 ml of 1M $KH_2PO_4$ add $ddH_2O$ to make up to 1 liter.
- Solution A 1 ml stock (stored at −20° C.): 131 μl of 1M Magnesium Chloride solution (Sigma, Cat No.:M1028) in 1 ml $ddH_2O$ to final concentration 66 mM.
- $NADP^+$ (Sigma, Cat No.: N0505, Mr 765.4) 43.5 mg, final concentration 50 mM.
- Hydrated salt of disodium D-Glucose-6-phosphate (Sigma, Cat No.: F7250, Mr 304.1) 172 mg, final concentration 500 mM.
- Solution B (stored at −20° C.): 17 U Glucose-6-phosphate dehydrogenase (Sigma, Cat No.: G6378, 250 U) in 340 μl of 5 mM sodium citrate (14.7 mg/ml) (trisbasic) (Sigma, cat No.: S46410).

MTT-Based P450 Reductase Assay Modified for Assessing Yeast-Derived Recombinant P450 Reductase Disposable cuvettes were used for this experiment. 850 μl of potassium phosphate buffer was added to a cuvette. 100 μg of yeast microsomes or 100 μg of cell supernatants containing the cytosolic fraction of yeast was added to the buffer followed by 10 μl of solution B. The contents were mixed gently to prevent any bubble formation in the resulting suspension. 10 μl of solution A was quickly added to the cuvette, and the contents were mixed by inverting a few times. The cuvette was quickly placed into the spectrophotometer together with the blank cuvette and its contents (that contained all components as in the other test cuvette but not the microsomes or cell supernatant) and the increase in the values at 610 nm was measured for a time period of 400 seconds. The electrons released from NADPH by recombinant P450 reductase enzyme were transferred to MTT, and the ability to reduce MTT was assessed spectrophotometrically by measuring the increase in A610 values as a result of the formation of blue formazan. The rate of MTT reduction was calculated from the change in A610 values using an extinction coefficient of 11.3 $mM^{-1}$ $cm^{-1}$ and the formula, $\Delta A610/min/11.3*0.1$ mg/ml=µmole reduced MTT/min/mg of protein.

Results

The results are shown in Table 3 below.

TABLE 3

Comparative MTT reducing ability of the different reductases.

| hRD Variant | µM of reduced MTT/min/mg of protein (Relative Rates) |
|---|---|
| hRD (SEQ ID NO: 6) | 1 |
| ΔN1hRD-M (SEQ ID NO: 9) | 2.5 ± 10% |
| ΔN1hRD-HDEL (SEQ ID NO: 3) | 3 ± 10% |
| ΔN2hRD-HDEL (SEQ ID NO: 4) | 3.5 ± 10% |

Conclusion

It seems that the new human P450 reductase variants have the potential to couple with a CYP better than the wild-type reductase.

EXAMPLE 11—CYTOCHROME P450 ASSAYS FOR MEASURING SPECIFIC ACTIVITIES

TABLE 4

Outline of the parameters used to analyse the activities of cytochrome P450 enzymes using a fluorescent plate reader (Bio-Tek Synergy HT).

| Enzyme | Substrate | Product | Bandwidth of filter | | Sensitivity | Final Substrate Conc. per reaction | Dilution of Substrate | Conc. of P450 per reaction (µl) |
|---|---|---|---|---|---|---|---|---|
| | | | Excitation | Emission | | | | |
| CYP1A1 | 7-Ethoxyresorufin | Resorufin | 530 nm | 590 nm | 55 | 5 µM | DMSO | 0.5 pmol |
| CYP1B1 | 7-Ethoxyresorufin | Resorufin | 530 nm | 590 nm | 60 | 5 µM | DMSO | 1.7 pmol |
| CYP1A2 | CEC | CHC | 400 nm | 460 nm | 80 | 16 µM | Acetonitrile | 2 pmol |
| CYP2D6 | EOMCC | CHC | 400 nm | 460 nm | 75 | 10 µM | Acetonitrile | 2.5 pmol |
| CYP3A4 | DBF | Fluorescein | 485 nm | 528 nm | 80 | 2 µM | Acetonitrile | 0.5 pmol |

CEC = 3-Cyano-7-Ethoxycoumarin;
EOMCC = Invitrogen ™;
DBF = Dibenzylfluorescein.
Protocols for enzyme assays The computer was switched on and the KC4 software (of the BioTek plate reader) was opened to select the parameters and plate layout. The plate reader machine was warmed to 37° C. 100 µM of stock solutions of the compounds were used to analyse the percentage inhibition of CYPs at a final concentration of 5 µM in each well.

45 µl of regenerating system was prepared and pre-warmed at 37° C. (see Table 5).

TABLE 5

The constitution of the regenerating system used per reaction in each single well for different CYPs was as follows.

| Enzyme | Solution A | Solution B | Inhibitor | KPi buffers | Water |
|---|---|---|---|---|---|
| CYP1A1 | 5 µl | 1 µl | 5 µl | 39 µl 0.2M | — |
| CYP1B1 | 5 µl | 1 µl | 5 µl | 39 µl 0.2M | — |
| CYP1A2 | 5 µl | 1 µl | 5 µl | 20 µl 0.5M | 19 µl |
| CYP2D6 | 5 µl | 1 µl | 5 µl | 25 µl 0.2M | 14 µl |
| CYP3A4 | 5 µl | 1 µl | 5 µl | 25 µl 0.2M | 14 µl |

50 µl of enzyme-substrate reaction mixture was prepared and kept in an incubator at 37° C. for 10 minutes (see Table 3).

TABLE 6

Enzyme-Substrate mixtures per reaction in each well were as follows.

| Enzyme | P450 Conc. | Control Microsome | Substrate | KPi buffer | Water |
|---|---|---|---|---|---|
| CYP1A1 | 0.5 µl | 2 µl | 5 µl 0.1 mM E.R | 42.5 µl 0.1M | — |
| CYP1B1 | 0.5 µl | 1.7 µl | 5 µl 0.1 mM E.R | 42.8 µl 0.1M | — |
| CYP1A2 | 1 µl | 1.6 µl | 5 µl 320 µM CEC | 42.4 µl 0.1M | — |
| CYP2D6 | 2.5 µl | 0.4 µl | 0.5 µl 2 mM EOMCC | 25 µl 0.2M | 21.6 µl |
| CYP3A4 | 1.1 µl | 0.102 µl | 0.1 µl 2 mM | 25 µl 0.2M | 23.96 µl |

In a well of a 96-well flat-bottomed microplate, 45 µl of regenerating system, 5 µl of 100 potential inhibitor (from the compound library) and 50 µl of enzyme/substrate mixture were added in all the wells except the wells which acted as negative controls. Instead of any compound, 5 µl of 10% DMSO was added to negative control wells. After preparation of the contents of all the wells, the microplate was vortexed for a few seconds so that contents were mixed well, in each well, and incubated at 37° C. for 10 minutes. After 10 minutes, 75 µl of Tris-acetonitrile (stop solution) was added to all wells using an 8-channel multi-channel pipette to stop the reaction. After that 50 µl of enzyme/substrate mixture was added into a negative well. The plate was left to shake for 10 seconds and endpoint assay was run using an appropriate setting (Table 4).

Reagents Used for Enzyme Activity/Inhibition Assays.

1 mM of 7-Ethoxyresorufin (ER), stored at −20° C.: MW of 7-ethoxyresorufin (ER), 241.2; 2.412 mg of ER in 100% DMSO. This solution was further diluted to 0.1 mM in 1% DMSO on the day of use.

10 mM 3-Cyano-7-ethoxycoumarin (CEC), stored at −20° C.: MW of CEC, 215.2; 2.152 mg of CEC in 100% acetonitrile. This was further diluted to 0.32 μM in 1% DMSO on the day of use.

2 mM 7-ethylmethyloxy-3-cyanocoumarin (EOMCC), stored at −20° C.: MW of EOMCC, 245.2; 0.1 mg of EOMCC in 100% acetonitrile.

2 mM Dibenzylfluorescein (DBF), stored at −20° C.: MW of DBF, 512.55; 2.06 mg of DBF in 100% acetonitrile.

100 mM (0.1 M) potassium phosphate buffer (KPi) at pH 7.4: 0.3 ml of 1.0 M $K_2HPO_4$+4.7 ml of 1.0 M $KH_2PO_4$ were mixed and made up to 50 ml with distilled water.

100 mM (0.2 M) potassium phosphate buffer (KPi) at pH 7.4: 0.6 ml of 1.0M $K_2HPO_4$+9.4 ml of 1.0M $KH_2PO_4$ were mixed and made up to 50 ml with distilled water.

500 mM (0.5 M) potassium phosphate buffer (KPi) at pH 7.4: 1.5 ml of 1.0 M $K_2HPO_4$+23.5 ml of 1.0 M $KH_2PO_4$ were mixed and made up to 50 ml with distilled water.

Solution A stored at −20° C.: 183 mg of $NADP^+$+183 mg of glucose-6-phosphate+654 μl of 1.0 M Magnesium chloride solution were mixed in a sterile tube containing 9.15 ml of distilled water and the mixture was aliquoted into 1.5 ml eppendorf tubes for storage at −20° C.

Solution B, stored at −20° C.: 250 Units of glucose-6-phosphate dehydrogenase+6.25 ml of 5 mM sodium citrate, mixed in a tube and made up to 10 ml with distilled water.

10% DMSO: 1 ml of 100% DMSO was diluted in 9 ml of distilled water and stored in a dark place at room temperature.

1% DMSO: 1 ml of 10% DMSO was diluted in 9 ml of distilled water and stored in a dark place.

Tris-acetonitrile (Stop solution): 100 ml of 0.5 M Tris-HCl+400 ml of 80% acetonitrile.

Results

TABLE 7

Comparative level of CYP2D6 enzyme produced using the different reductases.

| hRD Variant | pmoles of CYP2D6/mg of total protein (Relative Amounts) |
|---|---|
| hRD (SEQ ID NO: 6) | 1 |
| ΔN1hRD-M (SEQ ID NO: 9) | 4 ± 10% |
| ΔN1hRD-HDEL (SEQ ID NO: 3) | 6 ± 10% |
| ΔN2hRD-HDEL (SEQ ID NO: 4) | 6 ± 10% |

TABLE 7

Comparative level of CYP1A2 enzyme produced using the different reductases.

| hRD Variant | pmoles of CYP1A2/mg of total protein (Relative Amounts) |
|---|---|
| hRD (SEQ ID NO: 6) | 1 |
| ΔN1hRD-M (SEQ ID NO: 9) | 4 ± 10% |
| ΔN1hRD-HDEL (SEQ ID NO: 3) | 6 ± 10% |
| ΔN2hRD-HDEL (SEQ ID NO: 4) | 6 ± 10% |

Conclusion

It appears that the variant human P450 reductases have a far better ability to activate CYP2D6 and CYP1A2 than the wild-type enzyme.

While this invention has been particularly shown and described with references to preferred embodiments thereof, it will be understood by those skilled in the art that various changes in form and details may be made therein without departing from the scope of the invention encompassed by the appended claims.

The invention claimed is:

1. An isolated or recombinant polypeptide comprising or consisting of
    a modified P450 reductase, wherein the modified P450 reductase is a P450 reductase which lacks N-terminal amino acids relative to the corresponding wild type P450 reductase and comprises an epitope tag comprising the amino acid sequence HDEL (SEQ ID NO: 1), optionally wherein the amino acid sequence HDEL (SEQ ID NO: 1) is replaced by KDEL (SEQ ID NO: 2), and
    wherein the modified P450 reductase has the amino acid sequence of SEQ ID NO: 3 or SEQ ID NO: 4, or an amino acid sequence which has at least 90% sequence identity to the amino acid sequence of SEQ ID NO: 3 or SEQ ID NO: 4, and further wherein the modified P450 reductase, when co-expressed with a cytochrome P450, increases the activity and/or expression of the cytochrome P450 compared to the activity and/or expression of the cytochrome P450 when co-expressed with the wild type P450 reductase.

2. The polypeptide as claimed in claim 1, wherein the P450 reductase lacks N-terminal amino acids by being truncated at the N terminus.

3. The polypeptide as claimed in claim 2, wherein the truncation comprises the 24 N-terminal amino acids.

4. The polypeptide as claimed in claim 3, wherein the truncation comprises the 54 N-terminal amino acid acids.

5. The polypeptide as claimed in claim 1, wherein the epitope tag is linked to the C-terminal end of the polypeptide.

6. The polypeptide of claim 1, wherein the P450 reductase is a human P450 reductase.

7. The polypeptide of claim 1 wherein the P450 reductase is a yeast P450 reductase.

8. The polypeptide of claim 1, wherein the modified P450 reductase has an amino acid sequence which has at least 95% sequence identity to the amino acid sequence of SEQ ID NO: 3 or SEQ ID NO: 4.

* * * * *

SEQUENCE LISTING

<160> NUMBER OF SEQ ID NOS: 15

<210> SEQ ID NO 1
<211> LENGTH: 4
<212> TYPE: PRT
<213> ORGANISM: Artificial Sequence
<220> FEATURE:
<223> OTHER INFORMATION: Epitope tag

<400> SEQUENCE: 1

His Asp Glu Leu
1

<210> SEQ ID NO 2
<211> LENGTH: 4
<212> TYPE: PRT
<213> ORGANISM: Artificial Sequence
<220> FEATURE:
<223> OTHER INFORMATION: Epitope tag

<400> SEQUENCE: 2

Lys Asp Glu Leu
1

<210> SEQ ID NO 3
<211> LENGTH: 657
<212> TYPE: PRT
<213> ORGANISM: Artificial Sequence
<220> FEATURE:
<223> OTHER INFORMATION: delN1hRD-HDEL

<400> SEQUENCE: 3

```
Met Thr Asp Met Ile Leu Phe Ser Leu Ile Val Gly Leu Leu Thr Tyr
1               5                   10                  15

Trp Phe Leu Phe Arg Lys Lys Glu Glu Val Pro Glu Phe Thr Lys
            20                  25                  30

Ile Gln Thr Leu Thr Ser Ser Val Arg Glu Ser Ser Phe Val Glu Lys
                35                  40                  45

Met Lys Lys Thr Gly Arg Asn Ile Ile Val Phe Tyr Gly Ser Gln Thr
            50                  55                  60

Gly Thr Ala Glu Glu Phe Ala Asn Arg Leu Ser Lys Asp Ala His Arg
65                  70                  75                  80

Tyr Gly Met Arg Gly Met Ser Ala Asp Pro Glu Glu Tyr Asp Leu Ala
                85                  90                  95

Asp Leu Ser Ser Leu Pro Glu Ile Asp Asn Ala Leu Val Val Phe Cys
            100                 105                 110

Met Ala Thr Tyr Gly Glu Gly Asp Pro Thr Asp Asn Ala Gln Asp Phe
            115                 120                 125

Tyr Asp Trp Leu Gln Glu Thr Asp Val Asp Leu Ser Gly Val Lys Phe
            130                 135                 140

Ala Val Phe Gly Leu Gly Asn Lys Thr Tyr Glu His Phe Asn Ala Met
145                 150                 155                 160

Gly Lys Tyr Val Asp Lys Arg Leu Glu Gln Leu Gly Ala Gln Arg Ile
                165                 170                 175

Phe Glu Leu Gly Leu Gly Asp Asp Gly Asn Leu Glu Glu Asp Phe
            180                 185                 190

Ile Thr Trp Arg Glu Gln Phe Trp Pro Ala Val Cys Glu His Phe Gly
            195                 200                 205

Val Glu Ala Thr Gly Glu Glu Ser Ser Ile Arg Gln Tyr Glu Leu Val
            210                 215                 220

Val His Thr Asp Ile Asp Ala Ala Lys Val Tyr Met Gly Glu Met Gly
225                 230                 235                 240

Arg Leu Lys Ser Tyr Glu Asn Gln Lys Pro Pro Phe Asp Ala Lys Asn
                245                 250                 255

Pro Phe Leu Ala Ala Val Thr Thr Asn Arg Lys Leu Asn Gln Gly Thr
            260                 265                 270

Glu Arg His Leu Met His Leu Glu Leu Asp Ile Ser Asp Ser Lys Ile
            275                 280                 285

Arg Tyr Glu Ser Gly Asp His Val Ala Val Tyr Pro Ala Asn Asp Ser
            290                 295                 300

Ala Leu Val Asn Gln Leu Gly Lys Ile Leu Gly Ala Asp Leu Asp Val
305                 310                 315                 320

Val Met Ser Leu Asn Asn Leu Asp Glu Glu Ser Asn Lys Lys His Pro
                325                 330                 335

Phe Pro Cys Pro Thr Ser Tyr Arg Thr Ala Leu Thr Tyr Tyr Leu Asp
            340                 345                 350

Ile Thr Asn Pro Pro Arg Thr Asn Val Leu Tyr Glu Leu Ala Gln Tyr
            355                 360                 365
```

```
Ala Ser Glu Pro Ser Glu Gln Glu Leu Leu Arg Lys Met Ala Ser Ser
    370                 375                 380

Ser Gly Glu Gly Lys Glu Leu Tyr Leu Ser Trp Val Val Glu Ala Arg
385                 390                 395                 400

Arg His Ile Leu Ala Ile Leu Gln Asp Cys Pro Ser Leu Arg Pro Pro
                405                 410                 415

Ile Asp His Leu Cys Glu Leu Leu Pro Arg Leu Gln Ala Arg Tyr Tyr
            420                 425                 430

Ser Ile Ala Ser Ser Lys Val His Pro Asn Ser Val His Ile Cys
        435                 440                 445

Ala Val Val Val Glu Tyr Glu Thr Lys Ala Gly Arg Ile Asn Lys Gly
    450                 455                 460

Val Ala Thr Asn Trp Leu Arg Ala Lys Glu Pro Ala Gly Glu Asn Gly
465                 470                 475                 480

Gly Arg Ala Leu Val Pro Met Phe Val Arg Lys Ser Gln Phe Arg Leu
                485                 490                 495

Pro Phe Lys Ala Thr Thr Pro Val Ile Met Val Gly Pro Gly Thr Gly
            500                 505                 510

Val Ala Pro Phe Ile Gly Phe Ile Gln Glu Arg Ala Trp Leu Arg Gln
    515                 520                 525

Gln Gly Lys Glu Val Gly Glu Thr Leu Leu Tyr Tyr Gly Cys Arg Arg
530                 535                 540

Ser Asp Glu Asp Tyr Leu Tyr Arg Glu Glu Leu Ala Gln Phe His Arg
545                 550                 555                 560

Asp Gly Ala Leu Thr Gln Leu Asn Val Ala Phe Ser Arg Glu Gln Ser
                565                 570                 575

His Lys Val Tyr Val Gln His Leu Leu Lys Gln Asp Arg Glu His Leu
            580                 585                 590

Trp Lys Leu Ile Glu Gly Gly Ala His Ile Tyr Val Cys Gly Asp Ala
        595                 600                 605

Arg Asn Met Ala Arg Asp Val Gln Asn Thr Phe Tyr Asp Ile Val Ala
    610                 615                 620

Glu Leu Gly Ala Met Glu His Ala Gln Ala Val Asp Tyr Ile Lys Lys
625                 630                 635                 640

Leu Met Thr Lys Gly Arg Tyr Ser Leu Asp Val Trp Ser His Asp Glu
                645                 650                 655

Leu

<210> SEQ ID NO 4
<211> LENGTH: 628
<212> TYPE: PRT
<213> ORGANISM: Artificial Sequence
<220> FEATURE:
<223> OTHER INFORMATION: delN2hRD-HDEL

<400> SEQUENCE: 4

Met Thr Lys Ile Gln Thr Leu Thr Ser Ser Val Arg Glu Ser Ser Phe
1               5                   10                  15

Val Glu Lys Met Lys Lys Thr Gly Arg Asn Ile Ile Val Phe Tyr Gly
                20                  25                  30

Ser Gln Thr Gly Thr Ala Glu Phe Ala Asn Arg Leu Ser Lys Asp
            35                  40                  45

Ala His Arg Tyr Gly Met Arg Gly Met Ser Ala Asp Pro Glu Glu Tyr
        50                  55                  60

Asp Leu Ala Asp Leu Ser Ser Leu Pro Glu Ile Asp Asn Ala Leu Val
```

```
                65                  70                  75                  80
Val Phe Cys Met Ala Thr Tyr Gly Glu Gly Asp Pro Thr Asp Asn Ala
                85                  90                  95
Gln Asp Phe Tyr Asp Trp Leu Gln Glu Thr Asp Val Asp Leu Ser Gly
               100                 105                 110
Val Lys Phe Ala Val Phe Gly Leu Gly Asn Lys Thr Tyr Glu His Phe
               115                 120                 125
Asn Ala Met Gly Lys Tyr Val Asp Lys Arg Leu Glu Gln Leu Gly Ala
130                 135                 140
Gln Arg Ile Phe Glu Leu Gly Leu Gly Asp Asp Gly Asn Leu Glu
145                 150                 155                 160
Glu Asp Phe Ile Thr Trp Arg Glu Gln Phe Trp Pro Ala Val Cys Glu
               165                 170                 175
His Phe Gly Val Glu Ala Thr Gly Glu Glu Ser Ser Ile Arg Gln Tyr
               180                 185                 190
Glu Leu Val Val His Thr Asp Ile Asp Ala Ala Lys Val Tyr Met Gly
               195                 200                 205
Glu Met Gly Arg Leu Lys Ser Tyr Glu Asn Gln Lys Pro Pro Phe Asp
               210                 215                 220
Ala Lys Asn Pro Phe Leu Ala Ala Val Thr Thr Asn Arg Lys Leu Asn
225                 230                 235                 240
Gln Gly Thr Glu Arg His Leu Met His Leu Glu Leu Asp Ile Ser Asp
               245                 250                 255
Ser Lys Ile Arg Tyr Glu Ser Gly Asp His Val Ala Val Tyr Pro Ala
               260                 265                 270
Asn Asp Ser Ala Leu Val Asn Gln Leu Gly Lys Ile Leu Gly Ala Asp
               275                 280                 285
Leu Asp Val Val Met Ser Leu Asn Asn Leu Asp Glu Glu Ser Asn Lys
               290                 295                 300
Lys His Pro Phe Pro Cys Pro Thr Ser Tyr Arg Thr Ala Leu Thr Tyr
305                 310                 315                 320
Tyr Leu Asp Ile Thr Asn Pro Pro Arg Thr Asn Val Leu Tyr Glu Leu
               325                 330                 335
Ala Gln Tyr Ala Ser Glu Pro Ser Glu Gln Glu Leu Leu Arg Lys Met
               340                 345                 350
Ala Ser Ser Ser Gly Glu Gly Lys Glu Leu Tyr Leu Ser Trp Val Val
               355                 360                 365
Glu Ala Arg Arg His Ile Leu Ala Ile Leu Gln Asp Cys Pro Ser Leu
               370                 375                 380
Arg Pro Pro Ile Asp His Leu Cys Glu Leu Leu Pro Arg Leu Gln Ala
385                 390                 395                 400
Arg Tyr Tyr Ser Ile Ala Ser Ser Ser Lys Val His Pro Asn Ser Val
               405                 410                 415
His Ile Cys Ala Val Val Glu Tyr Glu Thr Lys Ala Gly Arg Ile
               420                 425                 430
Asn Lys Gly Val Ala Thr Asn Trp Leu Arg Ala Lys Glu Pro Ala Gly
               435                 440                 445
Glu Asn Gly Gly Arg Ala Leu Val Pro Met Phe Val Arg Lys Ser Gln
               450                 455                 460
Phe Arg Leu Pro Phe Lys Ala Thr Thr Pro Val Ile Met Val Gly Pro
465                 470                 475                 480
Gly Thr Gly Val Ala Pro Phe Ile Gly Phe Ile Gln Glu Arg Ala Trp
               485                 490                 495
```

```
Leu Arg Gln Gln Gly Lys Glu Val Gly Glu Thr Leu Leu Tyr Tyr Gly
            500                 505                 510

Cys Arg Arg Ser Asp Glu Asp Tyr Leu Tyr Arg Glu Leu Ala Gln
        515                 520                 525

Phe His Arg Asp Gly Ala Leu Thr Gln Leu Asn Val Ala Phe Ser Arg
        530                 535                 540

Glu Gln Ser His Lys Val Tyr Val Gln His Leu Leu Lys Gln Asp Arg
545                 550                 555                 560

Glu His Leu Trp Lys Leu Ile Glu Gly Ala His Ile Tyr Val Cys
                565                 570                 575

Gly Asp Ala Arg Asn Met Ala Arg Asp Val Gln Asn Thr Phe Tyr Asp
            580                 585                 590

Ile Val Ala Glu Leu Gly Ala Met Glu His Ala Gln Ala Val Asp Tyr
        595                 600                 605

Ile Lys Lys Leu Met Thr Lys Gly Arg Tyr Ser Leu Asp Val Trp Ser
        610                 615                 620

His Asp Glu Leu
625

<210> SEQ ID NO 5
<211> LENGTH: 2034
<212> TYPE: DNA
<213> ORGANISM: Artificial Sequence
<220> FEATURE:
<223> OTHER INFORMATION: Nucleic acid coding for delN1hRD-M protein
      (M = 12-amino acid c-myc tag)

<400> SEQUENCE: 5
ggatccaaaa aaatgactga tatgattttg ttctctttga ttgtcggttt gttaacatat     60
tggttcttgt ttaggaagaa gaaggaggag gtccctgagt ttacaaaaat tcagacattg    120
acatcatctg tcagagagtc ttcattcgtt gaaaagatga agaagacagg taggaatatt    180
atagttttct acggatctca gactggtact gcagaggagt tcgcaaacag gttgtctaag    240
gacgcacaca ggtacggtat gaggggaatg tcagcagacc ctgaggaata cgatttggct    300
gacttatctt ctttgccaga gattgacaac gctttagtcg tcttctgcat ggcaacatac    360
ggtgagggtg accctacaga caacgctcag gatttctacg actggttgca ggagacagac    420
gttgatttgt ctggtgtcaa attcgctgtt tttggattgg gaaataagac ttacgagcac    480
tttaacgcta tgggtaagta cgtcgacaaa aggttggaac agttaggtgc acagagaatt    540
ttcgaattgg gattgggtga cgacgatgga aacttggagg aggacttcat tacatggagg    600
gagcagttct ggccagctgt ctgtgaacat tcggtgtcg aggctactgg tgaagaatca    660
tcaataaggc agtacgagtt agtcgtccac acagacatag acgcagctaa ggtctacatg    720
ggtgaaatgg gtagattgaa gtcatatgaa aatcaaaaac caccattcga cgctaagaat    780
ccattcttgg cagcagtcac aacaaacagg aaattgaacc agggtactga gaggcatttg    840
atgcacttgg agttggacat atctgattca aaaattagat acgagtctgg agaccacgtc    900
gctgtctacc cagcaaatga ctctgcattg gtcaaccagt tgggaaagat tttgggtgca    960
gacttggacg tcgtcatgtc attgaacaac ttggatgaag agtctaacaa gaagcaccca   1020
ttcccatgcc caacttctta caggactgca ttaacatact acttagacat tactaaccca   1080
cctagaacaa atgtcttata cgaattggct cagtacgcat ctgaaccatc agagcaagag   1140
ttgttaagaa agatggcatc ttcttctggt gagggaaagg agttgtattt gtcttgggtc   1200
```

-continued

```
gttgaggcta gaaggcacat attggctata ttgcaggact gcccatcttt gaggcctcca    1260
atagaccact tatgcgagtt attacctaga ttgcaagcaa gatactattc tattgcttca    1320
tcatcaaagg ttcacccaaa ttctgtccac atatgcgctg tcgtcgtcga gtatgagact    1380
aaggctggaa gaataaataa gggtgtcgct acaaactggt taagggctaa ggagccagtc    1440
ggtgagaacg gaggtagagc tttggttcca atgttcgtca ggaaatcaca gttgaggttg    1500
cctttcaagg caacaacacc tgtcattatg gtcggtccag gtacaggttg gcacccttc     1560 attggtttta tacaggagag agcatggtta aggcagcagg gtaaggaagt cggtgaaact    1620
ttgttgtatt acggttgcag gaggtctgac gaggactact tgtataggga ggagttggct    1680
caattccaca gggacggtgc tttgacacaa ttgaacgttg catttagcag ggagcaatct    1740
cataaagttt atgttcaaca tttgttaaag caagacaggg agcacttgtg aagttgata    1800 gagggaggag ctcacatata cgtctgtgga gacgctagga acatggcaag ggacgtccag    1860
aatacatttt atgacattgt cgcagagttg ggtgcaatgg agcacgctca agcagttgat    1920
tatatcaaga agttgatgac taaaggtaga tactcattag acgtctggtc ttcatcagaa    1980
cagaagttaa tatctgagga agacttaaac ggttctaggt tgtaatagtc taga          2034
```

<210> SEQ ID NO 6
<211> LENGTH: 677
<212> TYPE: PRT
<213> ORGANISM: Homo sapiens

<400> SEQUENCE: 6

```
Met Gly Asp Ser His Val Asp Thr Ser Ser Thr Val Ser Glu Ala Val
1               5                   10                  15

Ala Glu Glu Val Ser Leu Phe Ser Met Thr Asp Met Ile Leu Phe Ser
            20                  25                  30

Leu Ile Val Gly Leu Leu Thr Tyr Trp Phe Leu Phe Arg Lys Lys Lys
        35                  40                  45

Glu Glu Val Pro Glu Phe Thr Lys Ile Gln Thr Leu Thr Ser Ser Val
    50                  55                  60

Arg Glu Ser Ser Phe Val Glu Lys Met Lys Lys Thr Gly Arg Asn Ile
65                  70                  75                  80

Ile Val Phe Tyr Gly Ser Gln Thr Gly Thr Ala Glu Glu Phe Ala Asn
                85                  90                  95

Arg Leu Ser Lys Asp Ala His Arg Tyr Gly Met Arg Gly Met Ser Ala
            100                 105                 110

Asp Pro Glu Glu Tyr Asp Leu Ala Asp Leu Ser Ser Leu Pro Glu Ile
        115                 120                 125

Asp Asn Ala Leu Val Val Phe Cys Met Ala Thr Tyr Gly Glu Gly Asp
    130                 135                 140

Pro Thr Asp Asn Ala Gln Asp Phe Tyr Asp Trp Leu Gln Glu Thr Asp
145                 150                 155                 160

Val Asp Leu Ser Gly Val Lys Phe Ala Val Phe Gly Leu Gly Asn Lys
                165                 170                 175

Thr Tyr Glu His Phe Asn Ala Met Gly Lys Tyr Val Asp Lys Arg Leu
            180                 185                 190

Glu Gln Leu Gly Ala Gln Arg Ile Phe Glu Leu Gly Leu Gly Asp Asp
        195                 200                 205

Asp Gly Asn Leu Glu Glu Asp Phe Ile Thr Trp Arg Glu Gln Phe Trp
    210                 215                 220

Pro Ala Val Cys Glu His Phe Gly Val Glu Ala Thr Gly Glu Glu Ser
```

-continued

```
            225                 230                 235                 240
        Ser Ile Arg Gln Tyr Glu Leu Val Val His Thr Asp Ile Asp Ala Ala
                        245                 250                 255
        Lys Val Tyr Met Gly Glu Met Gly Arg Leu Lys Ser Tyr Glu Asn Gln
                        260                 265                 270
        Lys Pro Pro Phe Asp Ala Lys Asn Pro Phe Leu Ala Ala Val Thr Thr
                        275                 280                 285
        Asn Arg Lys Leu Asn Gln Gly Thr Glu Arg His Leu Met His Leu Glu
                        290                 295                 300
        Leu Asp Ile Ser Asp Ser Lys Ile Arg Tyr Glu Ser Gly Asp His Val
        305                 310                 315                 320
        Ala Val Tyr Pro Ala Asn Asp Ser Ala Leu Val Asn Gln Leu Gly Lys
                        325                 330                 335
        Ile Leu Gly Ala Asp Leu Asp Val Val Met Ser Leu Asn Asn Leu Asp
                        340                 345                 350
        Glu Glu Ser Asn Lys Lys His Pro Phe Pro Cys Pro Thr Ser Tyr Arg
                        355                 360                 365
        Thr Ala Leu Thr Tyr Tyr Leu Asp Ile Thr Asn Pro Pro Arg Thr Asn
                        370                 375                 380
        Val Leu Tyr Glu Leu Ala Gln Tyr Ala Ser Glu Pro Ser Glu Gln Glu
        385                 390                 395                 400
        Leu Leu Arg Lys Met Ala Ser Ser Ser Gly Glu Gly Lys Glu Leu Tyr
                        405                 410                 415
        Leu Ser Trp Val Val Glu Ala Arg Arg His Ile Leu Ala Ile Leu Gln
                        420                 425                 430
        Asp Cys Pro Ser Leu Arg Pro Pro Ile Asp His Leu Cys Glu Leu Leu
                        435                 440                 445
        Pro Arg Leu Gln Ala Arg Tyr Tyr Ser Ile Ala Ser Ser Ser Lys Val
                        450                 455                 460
        His Pro Asn Ser Val His Ile Cys Ala Val Val Glu Tyr Glu Thr
        465                 470                 475                 480
        Lys Ala Gly Arg Ile Asn Lys Gly Val Ala Thr Asn Trp Leu Arg Ala
                        485                 490                 495
        Lys Glu Pro Ala Gly Glu Asn Gly Gly Arg Ala Leu Val Pro Met Phe
                        500                 505                 510
        Val Arg Lys Ser Gln Phe Arg Leu Pro Phe Lys Ala Thr Thr Pro Val
                        515                 520                 525
        Ile Met Val Gly Pro Gly Thr Gly Val Ala Pro Phe Ile Gly Phe Ile
                        530                 535                 540
        Gln Glu Arg Ala Trp Leu Arg Gln Gln Gly Lys Glu Val Gly Glu Thr
        545                 550                 555                 560
        Leu Leu Tyr Tyr Gly Cys Arg Arg Ser Asp Glu Asp Tyr Leu Tyr Arg
                        565                 570                 575
        Glu Glu Leu Ala Gln Phe His Arg Asp Gly Ala Leu Thr Gln Leu Asn
                        580                 585                 590
        Val Ala Phe Ser Arg Glu Gln Ser His Lys Val Tyr Val Gln His Leu
                        595                 600                 605
        Leu Lys Gln Asp Arg Glu His Leu Trp Lys Leu Ile Glu Gly Gly Ala
                        610                 615                 620
        His Ile Tyr Val Cys Gly Asp Ala Arg Asn Met Ala Arg Asp Val Gln
        625                 630                 635                 640
        Asn Thr Phe Tyr Asp Ile Val Ala Glu Leu Gly Ala Met Glu His Ala
                        645                 650                 655
```

```
Gln Ala Val Asp Tyr Ile Lys Lys Leu Met Thr Lys Gly Arg Tyr Ser
            660                 665                 670

Leu Asp Val Trp Ser
        675

<210> SEQ ID NO 7
<211> LENGTH: 653
<212> TYPE: PRT
<213> ORGANISM: Artificial Sequence
<220> FEATURE:
<223> OTHER INFORMATION: delN1hRD

<400> SEQUENCE: 7

Met Thr Asp Met Ile Leu Phe Ser Leu Ile Val Gly Leu Leu Thr Tyr
1               5                   10                  15

Trp Phe Leu Phe Arg Lys Lys Glu Glu Val Pro Glu Phe Thr Lys
            20                  25                  30

Ile Gln Thr Leu Thr Ser Ser Val Arg Glu Ser Ser Phe Val Glu Lys
            35                  40                  45

Met Lys Lys Thr Gly Arg Asn Ile Ile Val Phe Tyr Gly Ser Gln Thr
        50                  55                  60

Gly Thr Ala Glu Glu Phe Ala Asn Arg Leu Ser Lys Asp Ala His Arg
65                  70                  75                  80

Tyr Gly Met Arg Gly Met Ser Ala Asp Pro Glu Glu Tyr Asp Leu Ala
                85                  90                  95

Asp Leu Ser Ser Leu Pro Glu Ile Asp Asn Ala Leu Val Val Phe Cys
            100                 105                 110

Met Ala Thr Tyr Gly Glu Gly Asp Pro Thr Asp Asn Ala Gln Asp Phe
        115                 120                 125

Tyr Asp Trp Leu Gln Glu Thr Asp Val Asp Leu Ser Gly Val Lys Phe
    130                 135                 140

Ala Val Phe Gly Leu Gly Asn Lys Thr Tyr Glu His Phe Asn Ala Met
145                 150                 155                 160

Gly Lys Tyr Val Asp Lys Arg Leu Glu Gln Leu Gly Ala Gln Arg Ile
                165                 170                 175

Phe Glu Leu Gly Leu Gly Asp Asp Gly Asn Leu Glu Glu Asp Phe
            180                 185                 190

Ile Thr Trp Arg Glu Gln Phe Trp Pro Ala Val Cys Glu His Phe Gly
        195                 200                 205

Val Glu Ala Thr Gly Glu Glu Ser Ser Ile Arg Gln Tyr Glu Leu Val
    210                 215                 220

Val His Thr Asp Ile Asp Ala Ala Lys Val Tyr Met Gly Glu Met Gly
225                 230                 235                 240

Arg Leu Lys Ser Tyr Glu Asn Gln Lys Pro Pro Phe Asp Ala Lys Asn
                245                 250                 255

Pro Phe Leu Ala Ala Val Thr Thr Asn Arg Lys Leu Asn Gln Gly Thr
            260                 265                 270

Glu Arg His Leu Met His Leu Glu Leu Asp Ile Ser Asp Ser Lys Ile
        275                 280                 285

Arg Tyr Glu Ser Gly Asp His Val Ala Val Tyr Pro Ala Asn Asp Ser
    290                 295                 300

Ala Leu Val Asn Gln Leu Gly Lys Ile Leu Gly Ala Asp Leu Asp Val
305                 310                 315                 320

Val Met Ser Leu Asn Asn Leu Asp Glu Glu Ser Asn Lys Lys His Pro
                325                 330                 335
```

Phe Pro Cys Pro Thr Ser Tyr Arg Thr Ala Leu Thr Tyr Tyr Leu Asp
                340                 345                 350

Ile Thr Asn Pro Pro Arg Thr Asn Val Leu Tyr Glu Leu Ala Gln Tyr
                355                 360                 365

Ala Ser Glu Pro Ser Glu Gln Glu Leu Leu Arg Lys Met Ala Ser Ser
            370                 375                 380

Ser Gly Glu Gly Lys Glu Leu Tyr Leu Ser Trp Val Glu Ala Arg
385                 390                 395                 400

Arg His Ile Leu Ala Ile Leu Gln Asp Cys Pro Ser Leu Arg Pro Pro
                405                 410                 415

Ile Asp His Leu Cys Glu Leu Leu Pro Arg Leu Gln Ala Arg Tyr Tyr
                420                 425                 430

Ser Ile Ala Ser Ser Ser Lys Val His Pro Asn Ser Val His Ile Cys
            435                 440                 445

Ala Val Val Val Glu Tyr Glu Thr Lys Ala Gly Arg Ile Asn Lys Gly
            450                 455                 460

Val Ala Thr Asn Trp Leu Arg Ala Lys Glu Pro Ala Gly Glu Asn Gly
465                 470                 475                 480

Gly Arg Ala Leu Val Pro Met Phe Val Arg Lys Ser Gln Phe Arg Leu
                485                 490                 495

Pro Phe Lys Ala Thr Thr Pro Val Ile Met Val Gly Pro Gly Thr Gly
                500                 505                 510

Val Ala Pro Phe Ile Gly Phe Ile Gln Glu Arg Ala Trp Leu Gly Glu
            515                 520                 525

Asn Gly Gly Arg Ala Leu Val Pro Met Phe Val Arg Lys Ser Gln Phe
                530                 535                 540

Arg Leu Pro Phe Lys Ala Thr Thr Pro Val Ile Met Val Gly Pro Gly
545                 550                 555                 560

Thr Gly Val Ala Pro Phe Ile Gly Phe Ile Gln Glu Arg Ala Trp Leu
                565                 570                 575

His Lys Val Tyr Val Gln His Leu Leu Lys Gln Asp Arg Glu His Leu
                580                 585                 590

Trp Lys Leu Ile Glu Gly Ala His Ile Tyr Val Cys Gly Asp Ala
            595                 600                 605

Arg Asn Met Ala Arg Asp Val Gln Asn Thr Phe Tyr Asp Ile Val Ala
            610                 615                 620

Glu Leu Gly Ala Met Glu His Ala Gln Ala Val Asp Tyr Ile Lys Lys
625                 630                 635                 640

Leu Met Thr Lys Gly Arg Tyr Ser Leu Asp Val Trp Ser
                645                 650

<210> SEQ ID NO 8
<211> LENGTH: 624
<212> TYPE: PRT
<213> ORGANISM: Artificial Sequence
<220> FEATURE:
<223> OTHER INFORMATION: delN2hRD

<400> SEQUENCE: 8

Met Thr Lys Ile Gln Thr Leu Ser Ser Val Arg Glu Ser Ser Phe
1               5                   10                  15

Val Glu Lys Met Lys Lys Thr Gly Arg Asn Ile Ile Val Phe Tyr Gly
                20                  25                  30

Ser Gln Thr Gly Thr Ala Glu Glu Phe Ala Asn Arg Leu Ser Lys Asp
            35                  40                  45

```
Ala His Arg Tyr Gly Met Arg Gly Met Ser Ala Asp Pro Glu Glu Tyr
 50                  55                  60

Asp Leu Ala Asp Leu Ser Ser Leu Pro Glu Ile Asp Asn Ala Leu Val
 65                  70                  75                  80

Val Phe Cys Met Ala Thr Tyr Gly Glu Gly Asp Pro Thr Asp Asn Ala
                 85                  90                  95

Gln Asp Phe Tyr Asp Trp Leu Gln Glu Thr Asp Val Asp Leu Ser Gly
            100                 105                 110

Val Lys Phe Ala Val Phe Gly Leu Gly Asn Lys Thr Tyr Glu His Phe
        115                 120                 125

Asn Ala Met Gly Lys Tyr Val Asp Lys Arg Leu Glu Gln Leu Gly Ala
130                 135                 140

Gln Arg Ile Phe Glu Leu Gly Leu Gly Asp Asp Asp Gly Asn Leu Glu
145                 150                 155                 160

Glu Asp Phe Ile Thr Trp Arg Glu Gln Phe Trp Pro Ala Val Cys Glu
                165                 170                 175

His Phe Gly Val Glu Ala Thr Gly Glu Glu Ser Ser Ile Arg Gln Tyr
            180                 185                 190

Glu Leu Val Val His Thr Asp Ile Asp Ala Ala Lys Val Tyr Met Gly
        195                 200                 205

Glu Met Gly Arg Leu Lys Ser Tyr Glu Asn Gln Lys Pro Pro Phe Asp
210                 215                 220

Ala Lys Asn Pro Phe Leu Ala Ala Val Thr Thr Asn Arg Lys Leu Asn
225                 230                 235                 240

Gln Gly Thr Glu Arg His Leu Met His Leu Glu Leu Asp Ile Ser Asp
                245                 250                 255

Ser Lys Ile Arg Tyr Glu Ser Gly Asp His Val Ala Val Tyr Pro Ala
            260                 265                 270

Asn Asp Ser Ala Leu Val Asn Gln Leu Gly Lys Ile Leu Gly Ala Asp
        275                 280                 285

Leu Asp Val Val Met Ser Leu Asn Asn Leu Asp Glu Glu Ser Asn Lys
290                 295                 300

Lys His Pro Phe Pro Cys Pro Thr Ser Tyr Arg Thr Ala Leu Thr Tyr
305                 310                 315                 320

Tyr Leu Asp Ile Thr Asn Pro Pro Arg Thr Asn Val Leu Tyr Glu Leu
                325                 330                 335

Ala Gln Tyr Ala Ser Glu Pro Ser Glu Gln Glu Leu Leu Arg Lys Met
            340                 345                 350

Ala Ser Ser Ser Gly Glu Gly Lys Glu Leu Tyr Leu Ser Trp Val Val
        355                 360                 365

Glu Ala Arg Arg His Ile Leu Ala Ile Leu Gln Asp Cys Pro Ser Leu
370                 375                 380

Arg Pro Pro Ile Asp His Leu Cys Glu Leu Leu Pro Arg Leu Gln Ala
385                 390                 395                 400

Arg Tyr Tyr Ser Ile Ala Ser Ser Ser Lys Val His Pro Asn Ser Val
                405                 410                 415

His Ile Cys Ala Val Val Val Glu Tyr Glu Thr Lys Ala Gly Arg Ile
            420                 425                 430

Asn Lys Gly Val Ala Thr Asn Trp Leu Arg Ala Lys Glu Pro Ala Gly
        435                 440                 445

Glu Asn Gly Gly Arg Ala Leu Val Pro Met Phe Val Arg Lys Ser Gln
450                 455                 460
```

```
Phe Arg Leu Pro Phe Lys Ala Thr Thr Pro Val Ile Met Val Gly Pro
465                 470                 475                 480

Gly Thr Gly Val Ala Pro Phe Ile Gly Phe Ile Gln Glu Arg Ala Trp
            485                 490                 495

Leu Arg Gln Gln Gly Lys Glu Val Gly Glu Thr Leu Leu Tyr Tyr Gly
        500                 505                 510

Cys Arg Arg Ser Asp Glu Asp Tyr Leu Tyr Arg Glu Glu Leu Ala Gln
        515                 520                 525

Phe His Arg Asp Gly Ala Leu Thr Gln Leu Asn Val Ala Phe Ser Arg
        530                 535                 540

Glu Gln Ser His Lys Val Tyr Val Gln His Leu Leu Lys Gln Asp Arg
545                 550                 555                 560

Glu His Leu Trp Lys Leu Ile Glu Gly Ala His Ile Tyr Val Cys
            565                 570                 575

Gly Asp Ala Arg Asn Met Ala Arg Asp Val Gln Asn Thr Phe Tyr Asp
            580                 585                 590

Ile Val Ala Glu Leu Gly Ala Met Glu His Ala Gln Ala Val Asp Tyr
        595                 600                 605

Ile Lys Lys Leu Met Thr Lys Gly Arg Tyr Ser Leu Asp Val Trp Ser
610                 615                 620

<210> SEQ ID NO 9
<211> LENGTH: 670
<212> TYPE: PRT
<213> ORGANISM: Artificial Sequence
<220> FEATURE:
<223> OTHER INFORMATION: delN1hRD-M

<400> SEQUENCE: 9

Met Thr Asp Met Ile Leu Phe Ser Leu Ile Val Gly Leu Leu Thr Tyr
1               5                   10                  15

Trp Phe Leu Phe Arg Lys Lys Glu Glu Val Pro Glu Phe Thr Lys
            20                  25                  30

Ile Gln Thr Leu Thr Ser Ser Val Arg Glu Ser Ser Phe Val Glu Lys
        35                  40                  45

Met Lys Lys Thr Gly Arg Asn Ile Ile Val Phe Tyr Gly Ser Gln Thr
    50                  55                  60

Gly Thr Ala Glu Glu Phe Ala Asn Arg Leu Ser Lys Asp Ala His Arg
65                  70                  75                  80

Tyr Gly Met Arg Gly Met Ser Ala Asp Pro Glu Glu Tyr Asp Leu Ala
                85                  90                  95

Asp Leu Ser Ser Leu Pro Glu Ile Asp Asn Ala Leu Val Val Phe Cys
            100                 105                 110

Met Ala Thr Tyr Gly Glu Gly Asp Pro Thr Asp Asn Ala Gln Asp Phe
        115                 120                 125

Tyr Asp Trp Leu Gln Glu Thr Asp Val Asp Leu Ser Gly Val Lys Phe
130                 135                 140

Ala Val Phe Gly Leu Gly Asn Lys Thr Tyr Glu His Phe Asn Ala Met
145                 150                 155                 160

Gly Lys Tyr Val Asp Lys Arg Leu Glu Gln Leu Gly Ala Gln Arg Ile
                165                 170                 175

Phe Glu Leu Gly Leu Gly Asp Asp Asp Gly Asn Leu Glu Glu Asp Phe
            180                 185                 190

Ile Thr Trp Arg Glu Gln Phe Trp Pro Ala Val Cys Glu His Phe Gly
        195                 200                 205
```

```
Val Glu Ala Thr Gly Glu Glu Ser Ser Ile Arg Gln Tyr Glu Leu Val
210                 215                 220

Val His Thr Asp Ile Asp Ala Ala Lys Val Tyr Met Gly Glu Met Gly
225                 230                 235                 240

Arg Leu Lys Ser Tyr Glu Asn Gln Lys Pro Pro Phe Asp Ala Lys Asn
                245                 250                 255

Pro Phe Leu Ala Ala Val Thr Thr Asn Arg Lys Leu Asn Gln Gly Thr
            260                 265                 270

Glu Arg His Leu Met His Leu Glu Leu Asp Ile Ser Asp Ser Lys Ile
        275                 280                 285

Arg Tyr Glu Ser Gly Asp His Val Ala Val Tyr Pro Ala Asn Asp Ser
    290                 295                 300

Ala Leu Val Asn Gln Leu Gly Lys Ile Leu Gly Ala Asp Leu Asp Val
305                 310                 315                 320

Val Met Ser Leu Asn Asn Leu Asp Glu Glu Ser Asn Lys Lys His Pro
                325                 330                 335

Phe Pro Cys Pro Thr Ser Tyr Arg Thr Ala Leu Thr Tyr Tyr Leu Asp
                340                 345                 350

Ile Thr Asn Pro Pro Arg Thr Asn Val Leu Tyr Glu Leu Ala Gln Tyr
            355                 360                 365

Ala Ser Glu Pro Ser Glu Gln Glu Leu Leu Arg Lys Met Ala Ser Ser
370                 375                 380

Ser Gly Glu Gly Lys Glu Leu Tyr Leu Ser Trp Val Val Glu Ala Arg
385                 390                 395                 400

Arg His Ile Leu Ala Ile Leu Gln Asp Cys Pro Ser Leu Arg Pro Pro
                405                 410                 415

Ile Asp His Leu Cys Glu Leu Leu Pro Arg Leu Gln Ala Arg Tyr Tyr
            420                 425                 430

Ser Ile Ala Ser Ser Ser Lys Val His Pro Asn Ser Val His Ile Cys
        435                 440                 445

Ala Val Val Val Glu Tyr Glu Thr Lys Ala Gly Arg Ile Asn Lys Gly
    450                 455                 460

Val Ala Thr Asn Trp Leu Arg Ala Lys Glu Pro Ala Gly Glu Asn Gly
465                 470                 475                 480

Gly Arg Ala Leu Val Pro Met Phe Val Arg Lys Ser Gln Phe Arg Leu
                485                 490                 495

Pro Phe Lys Ala Thr Thr Pro Val Ile Met Val Gly Pro Gly Thr Gly
            500                 505                 510

Val Ala Pro Phe Ile Gly Phe Ile Gln Glu Arg Ala Trp Leu Arg Gln
        515                 520                 525

Gln Gly Lys Glu Val Gly Glu Thr Leu Leu Tyr Tyr Gly Cys Arg Arg
    530                 535                 540

Ser Asp Glu Asp Tyr Leu Tyr Arg Glu Glu Leu Ala Gln Phe His Arg
545                 550                 555                 560

Asp Gly Ala Leu Thr Gln Leu Asn Val Ala Phe Ser Arg Glu Gln Ser
                565                 570                 575

His Lys Val Tyr Val Gln His Leu Leu Lys Gln Asp Arg Glu His Leu
            580                 585                 590

Trp Lys Leu Ile Glu Gly Gly Ala His Ile Tyr Val Cys Gly Asp Ala
        595                 600                 605

Arg Asn Met Ala Arg Asp Val Gln Asn Thr Phe Tyr Asp Ile Val Ala
    610                 615                 620

Glu Leu Gly Ala Met Glu His Ala Gln Ala Val Asp Tyr Ile Lys Lys
```

| | 625 | | | 630 | | | 635 | | | 640 | |
|---|---|---|---|---|---|---|---|---|---|---|---|
|Leu|Met|Thr|Lys|Gly|Arg|Tyr|Ser|Leu|Asp|Val|Trp|Ser|Ser|Glu
| | | | |645| | | |650| | |655| | |

| | | | | | | | | | |
|---|---|---|---|---|---|---|---|---|---|
|Gln|Lys|Leu|Ile|Ser|Glu|Glu|Asp|Leu|Asn|Gly|Ser|Arg|Leu
| | | |660| | | |665| | | |670|

```
<210> SEQ ID NO 10
<211> LENGTH: 41
<212> TYPE: DNA
<213> ORGANISM: Artificial Sequence
<220> FEATURE:
<223> OTHER INFORMATION: ADH2 promoter sequence specific primers (5' PCR
      primer)

<400> SEQUENCE: 10
ccggtcgacg ccggcggcaa aacgtagggg caaacaaacg g                  41

<210> SEQ ID NO 11
<211> LENGTH: 38
<212> TYPE: DNA
<213> ORGANISM: Artificial Sequence
<220> FEATURE:
<223> OTHER INFORMATION: ADH2 promoter sequence specific primers (3' PCR
      primer)

<400> SEQUENCE: 11
cgggatccaa gctttgtgta ttacgatata gttaatag                      38

<210> SEQ ID NO 12
<211> LENGTH: 602
<212> TYPE: DNA
<213> ORGANISM: Artificial Sequence
<220> FEATURE:
<223> OTHER INFORMATION: ADH2 promoter

<400> SEQUENCE: 12
ccggtcgacg ccggcggcaa aacgtagggg caaacaaacg gaaaaatcgt ttctcaaatt    60
ttctgatgcc aagaactcta accagtctta tctaaaaatt gccttatgat ccgtctctcc   120
ggttacagcc tgtgtaactg attaatcctg cctttctaat caccattcta atgttttaat   180
taagggattt tgtcttcatt aacggctttc gctcataaaa atgttatgac gttttgcccg   240
caggcgggaa accatccact tcacgagact gatctcctct gccggaacac cgggcatctc   300
caacttataa gttggagaaa taagagaatt tcagattgag agaatgaaaa aaaaaaaaaa   360
aaaaaaggca gaggagagca tagaaatggg gttcactttt tggtaaagct atagcatgcc   420
tatcacatat aaatagagtg ccagtagcga cttttttcac actcgaaata ctcttactac   480
tgctctcttg ttgtttttat cacttcttgt ttcttcttgg taaatagaat atcaagctac   540
aaaaagcata caatcaacta tcaactatta actatatcgt aatacacaaa gcttggatcc   600
cg                                                                 602

<210> SEQ ID NO 13
<211> LENGTH: 1512
<212> TYPE: DNA
<213> ORGANISM: Homo sapiens

<400> SEQUENCE: 13
ggatccaaaa aaatgggggct agaagcactg gtgcccctgg ccgtgatagt ggccatcttc    60
ctgctcctgg tggacctgat gcaccggcgc aacgctgggg ctgcacgcta cccaccaggc   120 ccctgccac tgcccgggct gggcaacctg ctgcatgtgg acttccagaa cacaccatac   180
```

| | | |
|---|---|---|
| tgcttcgacc agttgcggcg ccgcttcggg gacgtgttca gcctgcagct ggcctggacg | 240 | |
| ccggtggtcg tgctcaatgg gctggcggcc gtgcgcgagg cgctggtgac ccacggcgag | 300 | |
| gacaccgccg accgcccgcc tgtgcccatc acccagatcc tgggtttcgg gccgcgttcc | 360 | |
| caagggtgt tcctggcgcg ctatgggccc gcgtggcgcg agcagaggcg cttctccgtg | 420 | |
| tccaccttgc gcaacttggg cctgggcaag aagtcgctgg agcagtgggt gaccgaggag | 480 | |
| gccgcctgcc tttgtgccgc cttcgccaac cactccggac gccccttcg ccccaacggt | 540 | |
| ctcttggaca aagccgtgag caacgtgatc gcctccctca cctgcgggcg ccgcttcgag | 600 | |
| tacgacgacc ctcgcttcct caggctgctg gacctagctc aggagggact gaaggaggag | 660 | |
| tcgggctttc tgcgcgaggt gctgaatgct gtccccgtcc tcctgcatat cccagcgctg | 720 | |
| gctggcaagg tcctacgctt ccaaaaggct ttcctgaccc agctggatga gctgctaact | 780 | |
| gagcacagga tgacctggga cccagcccag cccccccgag acctgactga ggccttcctg | 840 | |
| gcagagatga gaaggccaa ggggaacccct gagagcagct tcaatgatga aacctgcgc | 900 | |
| atagtggtgg ctgacctgtt ctctgccggg atggtgacca cctcgaccac gctggcctgg | 960 | |
| ggcctcctgc tcatgatcct acatccggat gtgcagcgcc gtgtccaaca ggagatcgac | 1020 | |
| gacgtgatag ggcaggtgcg cgcgaccaga gatgggtgacc aggctcacat gccctacacc | 1080 | |
| actgccgtga ttcatgaggt gcagcgcttt ggggacatcg tcccctggg tatgaccat | 1140 | |
| atgacatccc gtgacatcga agtacagggc ttccgcatcc taagggaac gacactcatc | 1200 | |
| accaacctgt catcggtgct gaaggatgag gccgtctggg agaagccctt ccgcttccac | 1260 | |
| cccgaacact tcctggatgc ccagggccac tttgtgaagc cggaggcctt cctgcctttc | 1320 | |
| tcagcaggcc gccgtgcatg cctcggggag ccctggcc gcatggagct cttcctcttc | 1380 | |
| ttcacctccc tgctgcagca cttcagcttc tcggtgccca ctggacagcc ccggcccagc | 1440 | |
| caccatggtg tctttgcttt cctggtgagc ccatcccct atgagctttg tgctgtgccc | 1500 | |
| cgctagtcta ga | 1512 | |

<210> SEQ ID NO 14
<211> LENGTH: 1573
<212> TYPE: DNA
<213> ORGANISM: Homo sapiens

<400> SEQUENCE: 14

| | | |
|---|---|---|
| atggatccaa aaaatggca ttgtcccagt ctgttccctt ctcggccaca gagcttctcc | 60 | |
| tggcctctgc catcttctgc ctggtattct gggtgctcaa gggtttgagg cctcgggtcc | 120 | |
| ccaaaggcct gaaaagtcca ccagagccat ggggctggcc cttgctcggg catgtgctga | 180 | |
| ccctggggaa gaaccgcac ctggcactgt caaggatgag ccagcgctac ggggacgtcc | 240 | |
| tgcagatccg cattggctcc acgcccgtgc tggtgctgag ccgcctggac accatccggc | 300 | |
| aggccctggt gcggcaggc gacgatttca agggccggcc tgacctctac acctccaccc | 360 | |
| tcatcactga tggccagagc ttgaccttca gcacagactc tggaccggtg tgggctgccc | 420 | |
| gccggcgcct ggcccagaat gccctcaaca ccttctccat cgcctctgac ccagcttcct | 480 | |
| catcctcctg ctacctggag gagcatgtga gcaaggaggc taaggccctg atcagcaggt | 540 | |
| tgcaggagct gatggcaggg cctgggcact cgaccctta caatcaggtg gtggtgtcag | 600 | |
| tggccaacgt cattggtgcc atgtgcttcg gacagcactt ccctgagagt agcgatgaga | 660 | |
| tgctcagcct cgtgaagaac actcatgagt cgtggagac tgcctcctcc gggaaccccc | 720 | |

```
tggacttctt ccccatcctt cgctacctgc ctaaccctgc cctgcagagg ttcaaggcct      780
tcaaccagag gttcctgtgg ttcctgcaga aaacagtcca ggagcactat caggactttg      840
acaagaacag tgtccgggac atcacggtg ccctgttcaa gcacagcaag aagggccta       900 gagccagcgg caacctcatc ccacaggaga agattgtcaa ccttgtcaat gacatctttg     960
gagcaggatt tgacacagtc accacagcca tctcctggag cctcatgtac cttgtgacca    1020
agcctgagat acagaggaag atccagaagg agctggacac tgtgattggc agggagcggc    1080
ggccccggct ctctgacaga ccccagctgc cctacttgga ggccttcatc ctggagacct    1140
tccgacactc ctccttcttg cccttcacca tcccccacag cacaacaagg gacacaacgc    1200
tgaatggctt ctacatcccc aagaaatgct gtgtcttcgt aaaccagtgg caggtcaacc    1260
atgacccaga gctgtgggag gaccctctg agttccggcc tgagcggttc ctcaccgccg     1320
atggcactgc cattaacaag cccttgagtg agaagatgat gctgtttggc atgggcaagc    1380
gccggtgtat cggggaagtc ctggccaagt gggagatctt cctcttcctg gccatcctgc    1440
tacagcaact ggagttcagc gtgccgccgg gcgtgaaagt cgacctgacc cccatctacg    1500
ggctgaccat gaagcacgcc cgctgtgaac atgtccaggc gcggctgcgc ttctccatca    1560
actgactcga gat                                                        1573

<210> SEQ ID NO 15
<211> LENGTH: 12
<212> TYPE: PRT
<213> ORGANISM: Artificial Sequence
<220> FEATURE:
<223> OTHER INFORMATION: c-myc epitope tag

<400> SEQUENCE: 15

Glu Gln Lys Leu Ile Ser Glu Glu Asp Leu Asn Gly
1               5                   10
```